(12) United States Patent
Kao et al.

(10) Patent No.: US 9,063,044 B2
(45) Date of Patent: Jun. 23, 2015

(54) MAGNETIC AGGREGATING AND WASHING DEVICE FOR IN VITRO ASSAYS AND METHODS OF USE THEREOF

(71) Applicant: PLEXBIO CO., LTD., Taipei (TW)

(72) Inventors: Chien-Teng Kao, Taipei (TW);
Yao-Kuang Chung, Taipei (TW);
Pei-San Lee, Taipei (TW)

(73) Assignee: PLEXBIO CO. LTD., Taipei (TW)

( * ) Notice: Subject to any disclaimer, the term of this patent is extended or adjusted under 35 U.S.C. 154(b) by 109 days.

(21) Appl. No.: 13/779,465

(22) Filed: Feb. 27, 2013

(65) Prior Publication Data

US 2014/0242614 A1  Aug. 28, 2014

(51) Int. Cl.
*G01N 33/543* (2006.01)
*G01N 1/34* (2006.01)
*B01L 9/00* (2006.01)
*G01N 35/00* (2006.01)

(52) U.S. Cl.
CPC .............. *G01N 1/34* (2013.01); *G01N 35/0098* (2013.01); *G01N 2035/00495* (2013.01); *B01L 9/523* (2013.01); *B01L 2200/0668* (2013.01); *B01L 2300/0829* (2013.01); *B01L 2400/0409* (2013.01); *B01L 2400/043* (2013.01)

(58) Field of Classification Search
CPC ............ B01L 9/523; B01L 2200/0668; B01L 2300/0829; B01L 2400/0409; B01L 2400/043; G01N 1/34; G01N 35/0098; G01N 2035/00495
USPC ......................................................... 436/526
See application file for complete search history.

(56) References Cited

U.S. PATENT DOCUMENTS 8,481,901 B2 * 7/2013 Bedingham et al. .......... 219/749
2009/0211956 A1 * 8/2009 Siddiqi .......................... 210/138

* cited by examiner

*Primary Examiner* — Bao Thuy L Nguyen
*Assistant Examiner* — Pensee Do
(74) *Attorney, Agent, or Firm* — Morrison & Foerster LLP

(57) ABSTRACT

Provided herein are magnetic aggregating and washing devices. Further provided herein are methods using magnetic aggregation to aggregate and wash sample molecules in an in vitro assay.

27 Claims, 16 Drawing Sheets

FIG. 16

Shaker parameters:

| Mixing rate | 100~1200 rpm |
|---|---|
| Orbit | 2mm |
| Temperature range | RT + 5°C ~ 70°C |
| Timing range | 1min ~ 99min59sec |
| Accuracy of the temperature | ≤0.5°C |
| Heating time | ≤25min (From room temperature TO 70°C) |
| Dimension (mm) | 280(D)×270(W)×140(H) |
| Net weight (kg) | 7.0 |

US 9,063,044 B2

MAGNETIC AGGREGATING AND WASHING DEVICE FOR IN VITRO ASSAYS AND METHODS OF USE THEREOF

FIELD

The present disclosure relates generally to the field of in vitro assays. In particular, the present disclosure relates to magnetic aggregation and washing of samples in in vitro assays.

BACKGROUND

High-throughput assays are becoming increasingly common in biotechnology and chemical analysis sectors. Advances in high-throughput DNA sequencing technology, protein analysis, and compound screening are driving a need for high-throughput processing of samples to isolate molecules of interest. The rise of companion diagnostics and the increased frequency of in vitro assays are further driving this need.

Raw processing of a sample, such as a cell or a tissue, to isolate and/or detect a molecule of interest often results in undesirable components remaining in the processed sample. For example, miscellaneous cellular debris and unwanted substances and molecules often remain following processing of biological samples. To remove these unwanted substances, processed samples are generally subjected to a series of washing procedures so that the molecule of interest is substantially free of any undesirable products present in the processed sample. Washing of the molecule often results in a reduced yield of the molecule from the sample, as the washing steps often wash away some fraction of the molecule of interest as well as the undesirable products.

Thus, there exists a need for efficient devices and methods for aggregation and washing of a sample that are compatible with methods of high-throughput processing of samples and that result in a high recovery yield of a molecule of interest.

BRIEF SUMMARY

The present disclosure relates to a device for washing a sample in an assay. In some embodiments, the device comprises: a) a magnetic structure configured to hold a microtiter plate where the microtiter plate is configured to sit on top of the magnetic structure; and, b) a motor operatively coupled to the magnetic structure wherein operation of the motor causes the microtiter plate and the magnetic structure to move together, wherein the movement produces a relative centrifugal force on the microtiter plate, wherein the magnetic structure comprises a plurality of magnets each having a first pole and a second pole, the first pole and the second pole having opposite magnetic properties, and wherein a first magnet of the magnetic structure and a second magnet of the magnetic structure are oriented in the magnetic structure such that the first pole of the first magnet faces the first pole of the second magnet, the first magnet adjacent to the second magnet in the magnetic structure.

In some embodiments, the movement of the microtiter plate and the magnetic structure is rotation. In some embodiments that may be combined with any of the preceding embodiments, a well in the microtiter plate is configured to contain a plurality of magnetic beads. In some embodiments that may be combined with any of the preceding embodiments, the device further comprises an aspirator configured to remove a portion of the content of a well of the microtiter plate from the well of the microtiter plate. In some embodiments that may be combined with any of the preceding embodiments, the device further comprises a controller adapted to operate the motor at a first speed for a first duration followed by a second speed for a second duration, the first speed higher than the second speed. In some embodiments that may be combined with any of the preceding embodiments, the first speed is in the range of about 800 rotations per minute to about 1,250 rotations per minute. In some embodiments that may be combined with any of the preceding embodiments, the first duration is in the range of about 20 seconds to about 40 seconds. In some embodiments that may be combined with any of the preceding embodiments, the first speed is in the range of about 800 rotations per minute to about 1,250 rotations per minute and the first duration is in the range of about 20 seconds to about 40 seconds. In some embodiments that may be combined with any of the preceding embodiments, the second speed is in the range of about 400 rotations per minute to about 600 rotations per minute. In some embodiments that may be combined with any of the preceding embodiments, the second duration is in the range of about 50 seconds to about 70 seconds. In some embodiments that may be combined with any of the preceding embodiments, the second speed is in the range of about 400 rotations per minute to about 600 rotations per minute and the second duration is in the range of about 50 seconds to about 70 seconds.

The present disclosure further relates to a method for washing a sample in an assay. In some embodiments, the method comprises: a) coupling a microtiter plate with a magnetic structure wherein the microtiter plate sits on top of the magnetic structure, wherein the microtiter plate contains a well comprising a sample and a plurality of magnetic beads, wherein the magnetic structure comprises a plurality of magnets each having a first pole and a second pole, the first pole and the second pole having opposite magnetic properties, and wherein a first magnet of the magnetic structure and a second magnet of the magnetic structure are oriented in the magnetic structure such that the first pole of the first magnet faces the first pole of the second magnet, the first magnet adjacent to the second magnet in the magnetic structure; b) rotating the microtiter plate such that the microtiter plate and the magnetic structure move together at a first speed for a first duration to distribute the plurality of magnetic beads in the well; and, c) rotating the microtiter plate such that the microtiter plate and the magnetic structure move together at a second speed for a second duration to aggregate a majority of the plurality of magnetic beads at a portion of the well, the second speed different from the first speed.

In some embodiments, the first speed is in the range of about 800 rotations per minute to about 1,250 rotations per minute. In some embodiments that may be combined with any of the preceding embodiments, the first duration is in the range of about 20 seconds to about 40 seconds. In some embodiments that may be combined with any of the preceding embodiments, the first speed is in the range of about 800 rotations per minute to about 1,250 rotations per minute and the first duration is in the range of about 20 seconds to about 40 seconds. In some embodiments that may be combined with any of the preceding embodiments, the rotation of the microtiter plate at the first speed produces a relative centrifugal force that exceeds the magnetic force between the magnetic beads in a well of the microtiter plate and the magnetic structure. In some embodiments that may be combined with any of the preceding embodiments, the second speed is in the range of about 400 rotations per minute to about 600 rotations per minute. In some embodiments that may be combined with any of the preceding embodiments, the second duration is in the range of about 50 seconds to about 70 seconds. In some embodiments that may be combined with any of the preceding embodiments, the second speed is in the range of about 400 rotations per minute to about 600 rotations per minute and the second duration is in the range of about 50 seconds to about 70 seconds. In some embodiments that may be combined with any of the preceding embodiments, the rotation of the microtiter plate at the second speed produces a relative centrifugal force that does not exceed the magnetic force between the magnetic beads in a well of the microtiter plate and the magnetic structure. In some embodiments that may be combined with any of the preceding embodiments, the method involves removing a portion of the contents in the well of the microtiter plate from the well of the microtiter plate following rotating the microtiter plate at the second speed for the second duration. In some embodiments that may be combined with any of the preceding embodiments, the portion of the well in which the majority of magnetic beads are aggregated is a first portion of the well and the contents are removed from a second portion of the well away from the first portion. In some embodiments that may be combined with any of the preceding embodiments, the sample is a biological sample. In some embodiments that may be combined with any of the preceding embodiments, the biological sample is a blood sample. In some embodiments that may be combined with any of the preceding embodiments, the biological sample contains a nucleic acid or a protein. In some embodiments that may be combined with any of the preceding embodiments, an agent that specifically binds to a nucleic acid or a protein in the sample is immobilized to the surface of a magnetic bead.

The present disclosure further relates to a magnetic structure for use in a magnetic aggregating device, wherein the magnetic structure is configured to hold, on its top, a microtiter plate, and wherein the magnetic structure comprises a plurality of magnets each having a first pole and a second pole, the first pole and the second pole having opposite magnetic properties, and wherein a first magnet of the magnetic structure and a second magnet of the magnetic structure are oriented in the magnetic structure such that the first pole of the first magnet faces the first pole of the second magnet, the first magnet adjacent to the second magnet in the magnetic structure. In some embodiments, the magnetic structure is configured to operatively couple to a motor.

DESCRIPTION OF THE FIGURES

FIG. 1B, right side, illustrates the distribution of a ferromagnetic material in the presence of two magnets with like poles facing each other.

FIG. 4).

FIG. 13A depicts a microtiter plate. FIG. 13B illustrates a magnetic plate, which is a magnetic structure, that is configured to hold the microtiter plate shown in FIG. 13A. FIG. 13C illustrates a shaker that is configured to hold the magnetic plate shown in FIG. 13B.

FIG. 15A and FIG. 15C illustrate schematics of side views of an exemplary embodiment of a magnetic structure. FIG. 15B illustrates a schematic of the top view of an exemplary embodiment of a magnetic structure. FIG. 15D illustrates a schematic of the bottom view of an exemplary embodiment of a magnetic structure. Measurement values are presented in millimeter (mm) units of length.

FIG. 16 illustrates a table describing various exemplary parameters associated with a magnetic aggregating device.

DETAILED DESCRIPTION

Figure 1:
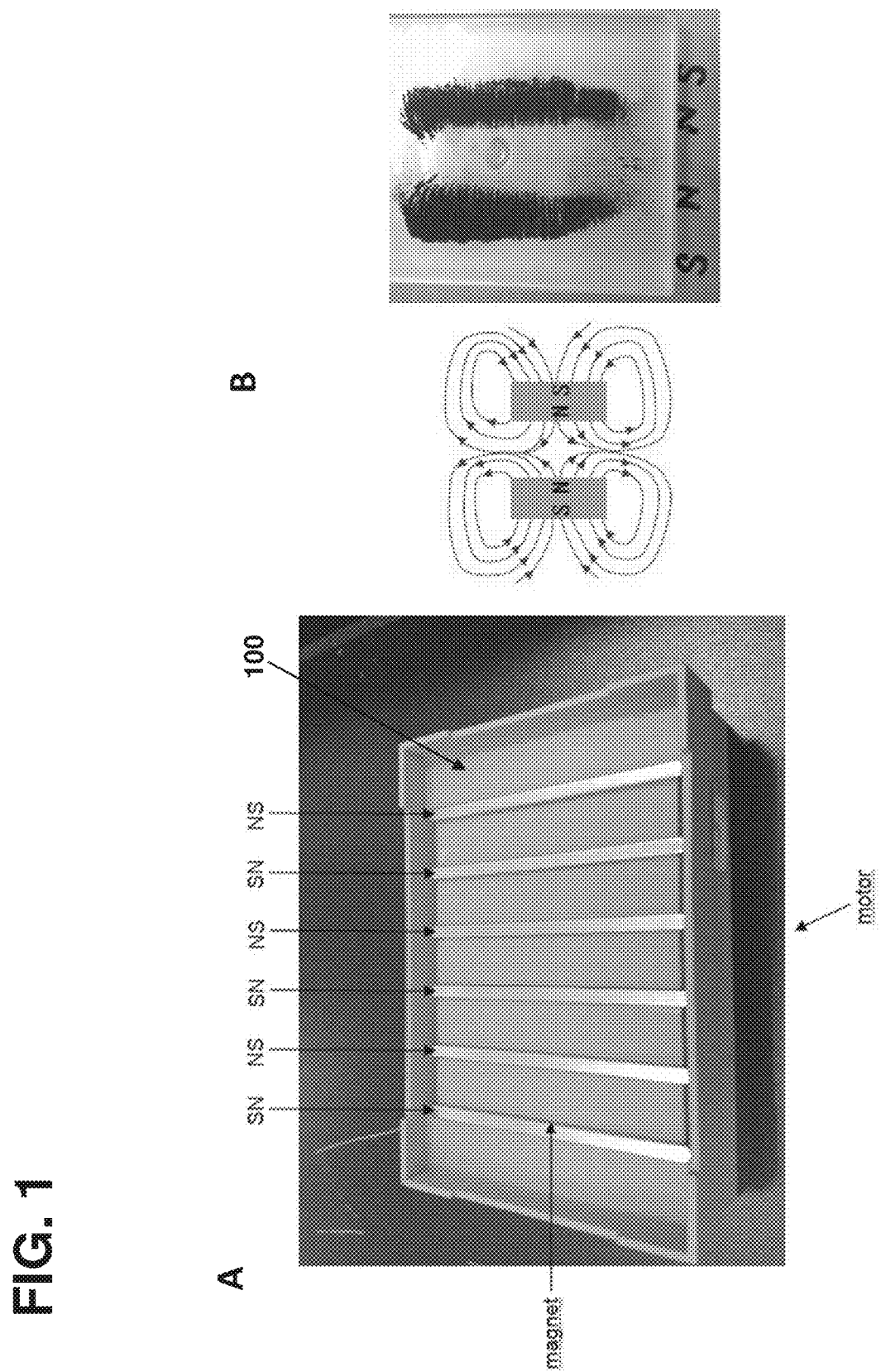
FIG. 1A illustrates a top angular view of an exemplary embodiment of a magnetic structure.
FIG. 1B, left side, illustrates the magnetic forces generated by two magnets with like poles facing each other, as shown in FIG. 1A.

The following description is presented to enable a person of ordinary skill in the art to make and use the various embodiments. Descriptions of specific devices, techniques, methods, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to the use of magnetic fields to facilitate the aggregation and washing of sample molecules in an in vitro assay.

Applicants have found that a particular arrangement of magnetic poles in a magnetic plate can be used beneficially to wash samples in in vitro assays. Controlled rotations of a microtiter plate, whose wells contain magnetic beads, on top of a magnetic plate facilitates both the washing and aggregation of the magnetic beads. Following rotation, magnetic beads in the wells of the microtiter plate become aggregated, meaning that in an exemplary well the beads in that well are aggregated at a specific portion of the well. In particular, the magnetic aggregation of magnetic beads resulted in effective washing and effective recovery (e.g. 80% recovery yield) of magnetic beads following multiple washing and aggregation steps.

DEFINITIONS

Unless defined otherwise, all scientific and technical terms are understood to have the same meaning as commonly used in the art to which they pertain. For the purpose of the present disclosure, the following terms are defined.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The use of the term "about" with regard to a numerical value is to be construed as including a value within the range of standard experimental or mechanical error. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments of the disclosure and does not pose a limitation on the scope of the disclosure unless otherwise claimed. No language in the specification should be construed as indicating any non-claimed element as essential to the practice of the embodiments of the disclosure.

Devices for Magnetic Aggregation and Washing

FIG. 1A depicts an exemplary embodiment of a magnetic structure for use in a magnetic aggregating device. As shown, the exemplary magnetic structure is magnetic plate 100, which is configured to hold a microtiter plate. Magnetic plate 100 contains a number of magnets. Each magnet has a north pole and a south pole, with the two different poles having opposite magnetic properties, each pole spanning the longitudinal axis of the magnet. "SN" and "NS" refer to the particular magnetic pole present along the longitudinal axis of a magnet; "SN" refers to a magnet having a southern pole on the left length of the magnet and a northern pole on the right length of the magnet, while "NS" refers to a magnet having a northern pole on the left length of the magnet and a southern pole on the right length of the magnet. In the exemplary embodiment shown in FIG. 1A, the magnets are arranged such that the first pole of a first magnet faces the first pole of a second magnet: SN-NS-SN-NS-SN-NS. Note that other arrangements of the magnetic poles of the magnets are possible such as, for example: NS-SN-NS-SN-NS-SN.

The magnet arrangement and the resulting magnetic field generated between two adjacent magnets in the magnetic plate is further illustrated in FIG. 1B. As the like poles of two separate magnets face each other, the result is a repulsive magnetic force between the two like poles. A magnetic material, such as the ferromagnetic material shown on the right hand side of FIG. 1B, is influenced by the repulsive magnetic force such that the magnetic material aggregates away from the repulsive magnetic force.

In a magnetic aggregating device, the magnetic structure is operatively coupled to a motor. In an exemplary embodiment, magnetic plate 100 is operatively coupled to a motor as outlined in FIG. 1A. Operation of the motor induces rotational movement of the magnetic plate. The rotational movement produces a relative centrifugal force on objects coupled to the magnetic plate, such as a microtiter plate.

Figure 2:
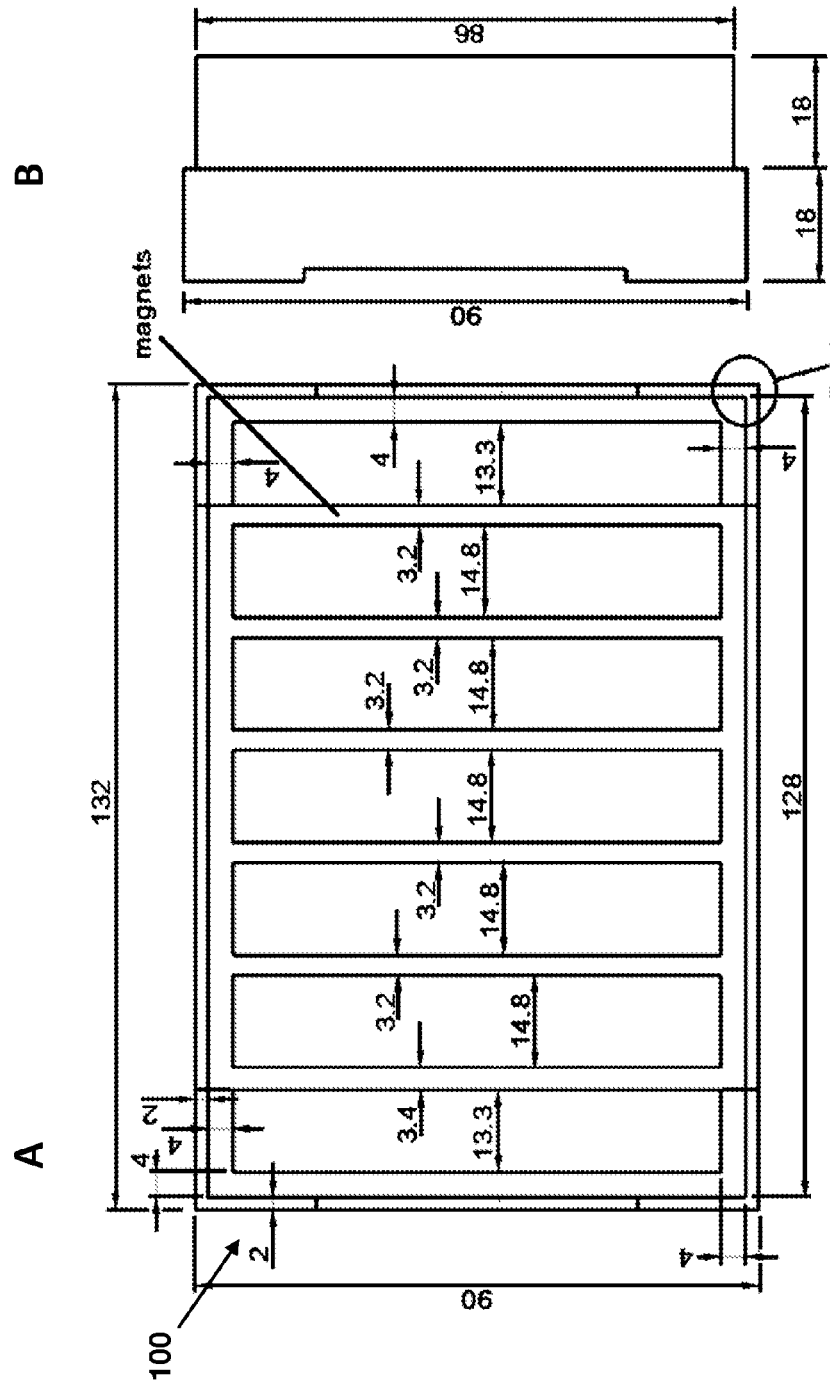
FIG. 2A illustrates a schematic of the top view of an exemplary embodiment of a magnetic structure.
FIG. 2B illustrates a schematic of a side view of an exemplary embodiment of a magnetic structure. Measurement values are presented in millimeter (mm) units of length.
Figure 3:
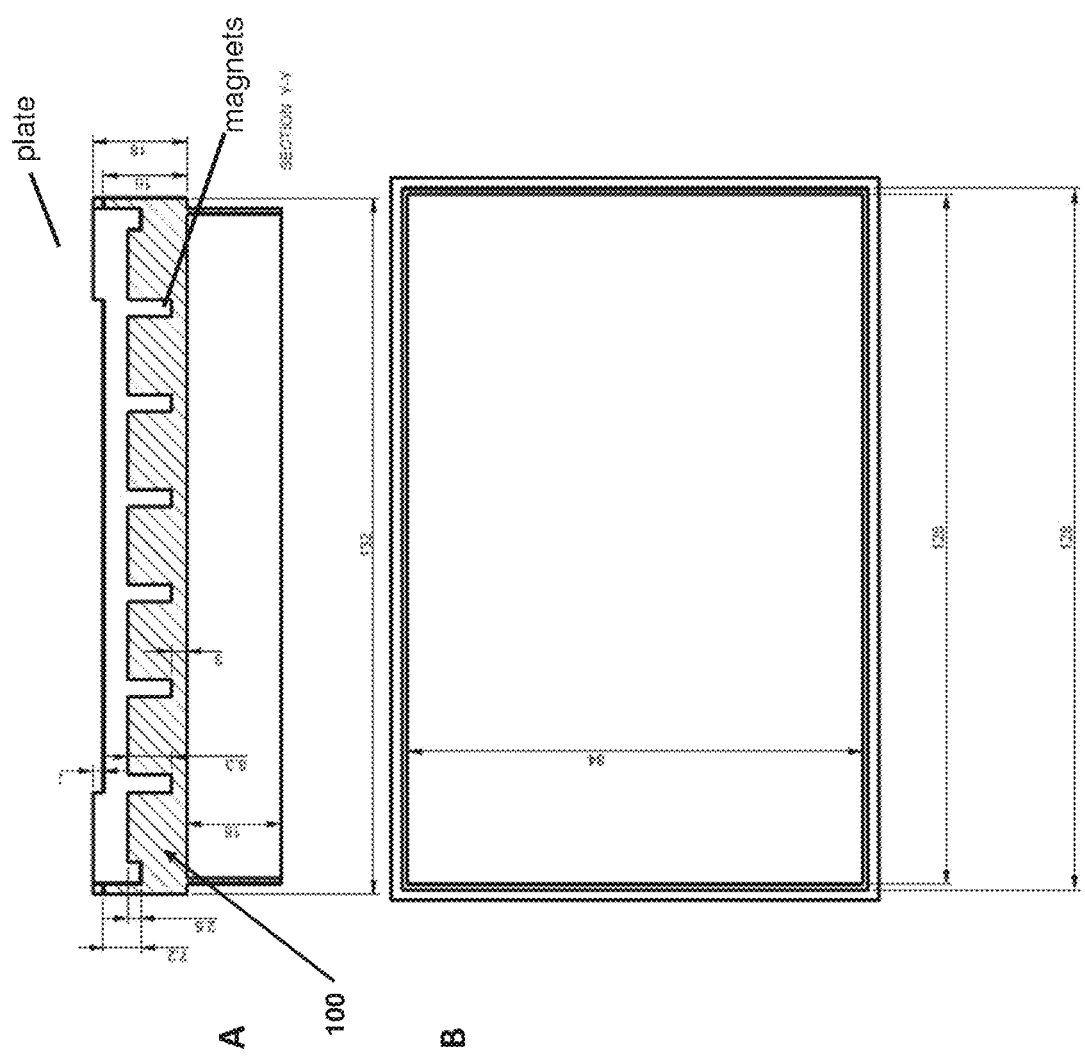
FIG. 3A illustrates a schematic of the front view of an exemplary embodiment of a magnetic structure.
FIG. 3B illustrates a schematic of the bottom view of an exemplary embodiment of a magnetic structure. Measurement values are presented in millimeter (mm) units of length.
Figure 15:
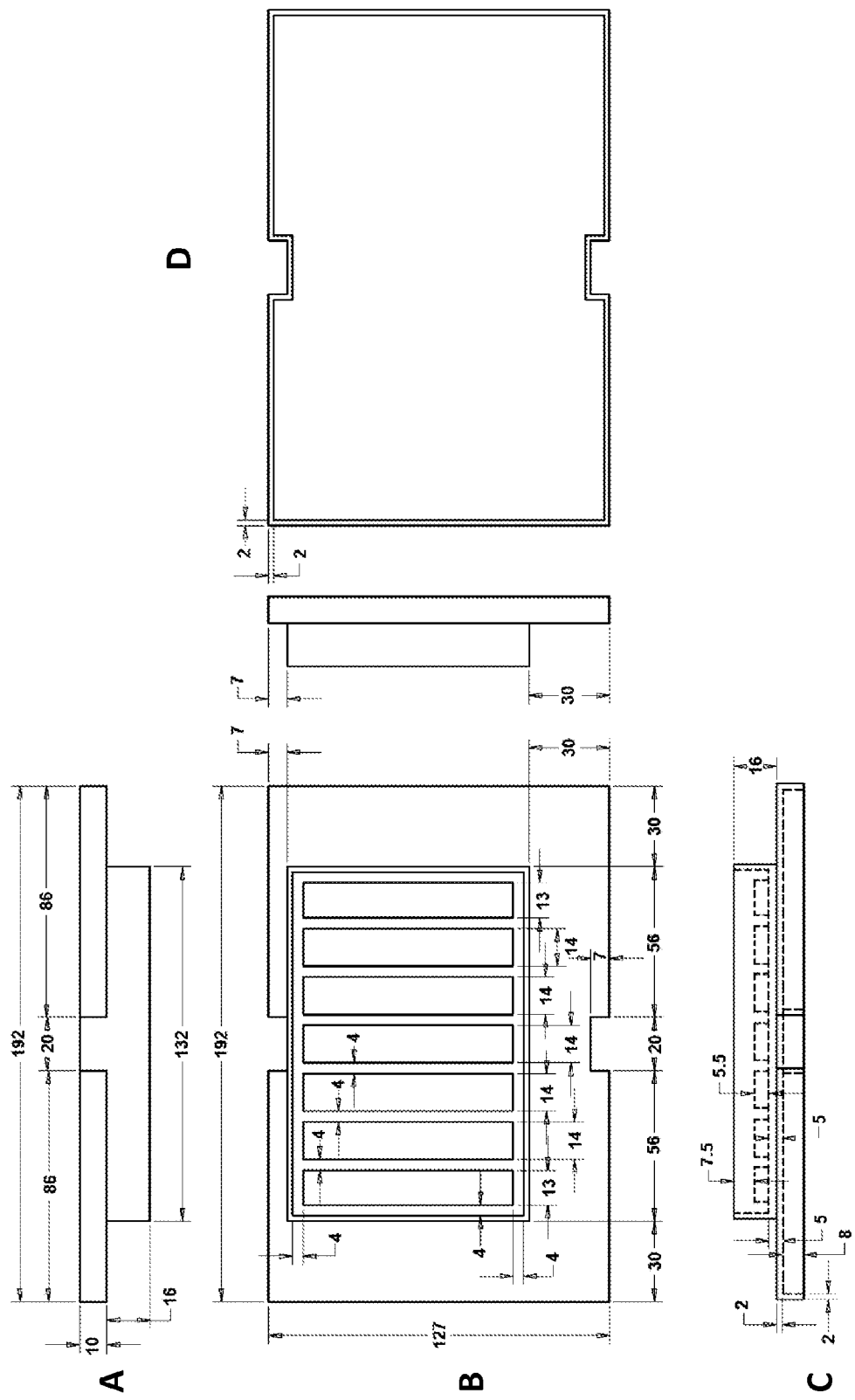
FIG. 15 illustrates a schematic of various views of an exemplary embodiment of a magnetic structure.

FIG. 2A is a top view of exemplary magnetic plate 100 shown in FIG. 1A. As shown, magnetic plate 100 is 128 mm in length and 90 mm wide, with the dimensions facilitating the placement of a microtiter plate on top of the magnetic plate. Note that other dimensions of the magnetic plate are possible. For example, FIG. 15 depicts various views of an additional exemplary magnetic structure that is different from magnetic plate 100. FIG. 2B is a side view of exemplary magnetic plate 100 shown in FIG. 1A. FIG. 3A is a front view of the exemplary magnetic plate shown in FIG. 1A. A number of magnets are present on the magnetic plate, with each magnet sitting inside an indentation in the magnetic plate. As shown, each magnet in magnetic plate 100 has dimensions of 82 mm (length)×8 mm (width)×4 mm (height). Note that other dimensions of magnets are possible so long as the dimensions are compatible with the dimensions of the magnetic plate. FIG. 3B is a bottom view of the exemplary magnetic plate shown in FIG. 1A.

Figure 4:
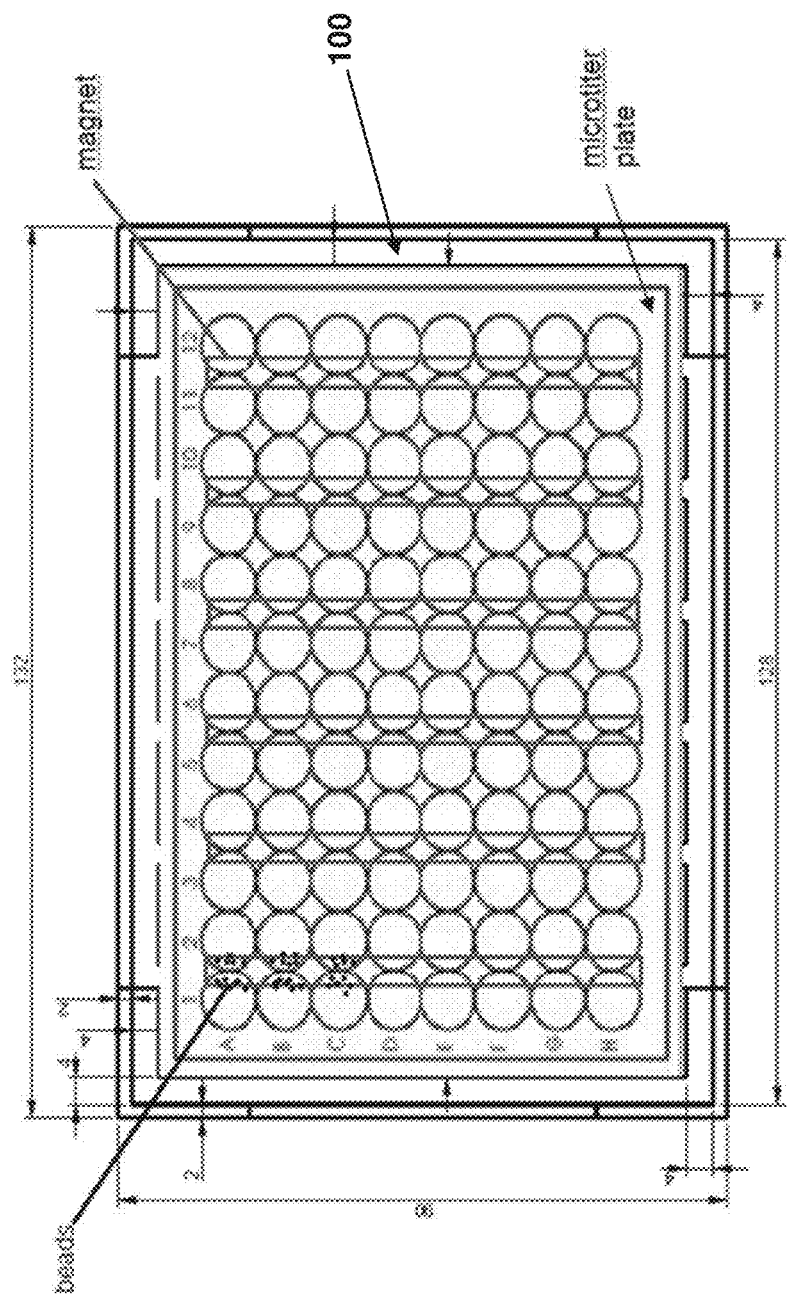
FIG. 4 illustrates a schematic of the top view of an exemplary embodiment of a magnetic structure holding a microtiter plate. Measurement values are presented in millimeter (mm) units of length.

FIG. 4 is a top view of exemplary magnetic plate 100 shown in FIG. 1A holding a microtiter plate. Magnetic plate 100 is configured to hold a microtiter plate such that the microtiter plate sits on top of the magnetic plate. Note that the dimensions of the magnetic plate and the microtiter plate may vary so long as the microtiter plate is capable of sitting on top of the magnetic plate.

Figure 14:
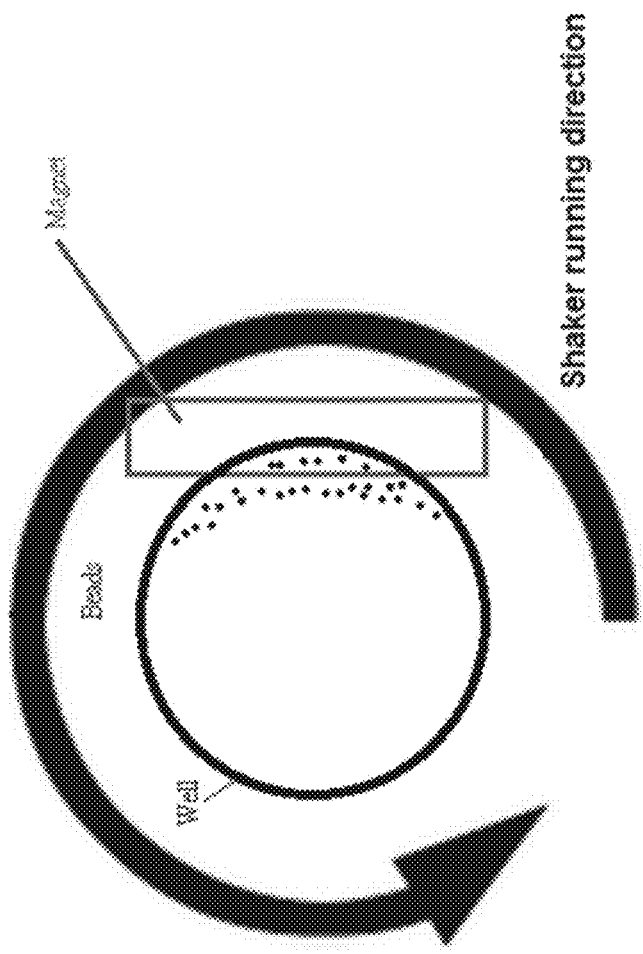
FIG. 14 illustrates a graphical depiction of the distribution of magnetic beads inside a well of a microtiter plate following rotation of the plate at a low-speed rotation in a magnetic aggregating device.

Magnetic beads are illustrated in the wells of the microtiter plate shown in FIG. 4 in the fashion observed after rotating the microtiter plate on top of the magnetic plate at 500 RPM. Following rotation at this speed, magnetic beads in the wells of the microtiter plate become aggregated, meaning that in an exemplary well the beads in that well are aggregated at a specific portion of the well. The location of the aggregated magnetic beads in a well is determined both by the magnetic force between the magnetic beads and the magnetic plate as well as the centrifugal force produced during the rotation. The aggregation of magnetic beads in a well of a microtiter plate following low-speed rotation of the microtiter plate on a magnetic plate is further illustrated in a graphical depiction in FIG. 14.

As shown in FIG. 4, the microtiter plate is positioned on top of magnetic plate 100 such that a portion of each well in the microtiter plate is above one of the magnets in the magnetic plate. This positioning allows a magnet on magnetic plate 100 positioned below a series of wells to exert a magnetic force on the magnetic beads in those wells with a portion of the well positioned above that magnet. Magnetic beads in all wells of the microtiter plate are thus capable of being influenced by a magnetic force. Note that other arrangements of microtiter plates, magnets in a magnetic plate, and positional relationships between wells in a microtiter plate and magnets on a magnetic plate are also possible.

Figure 13:
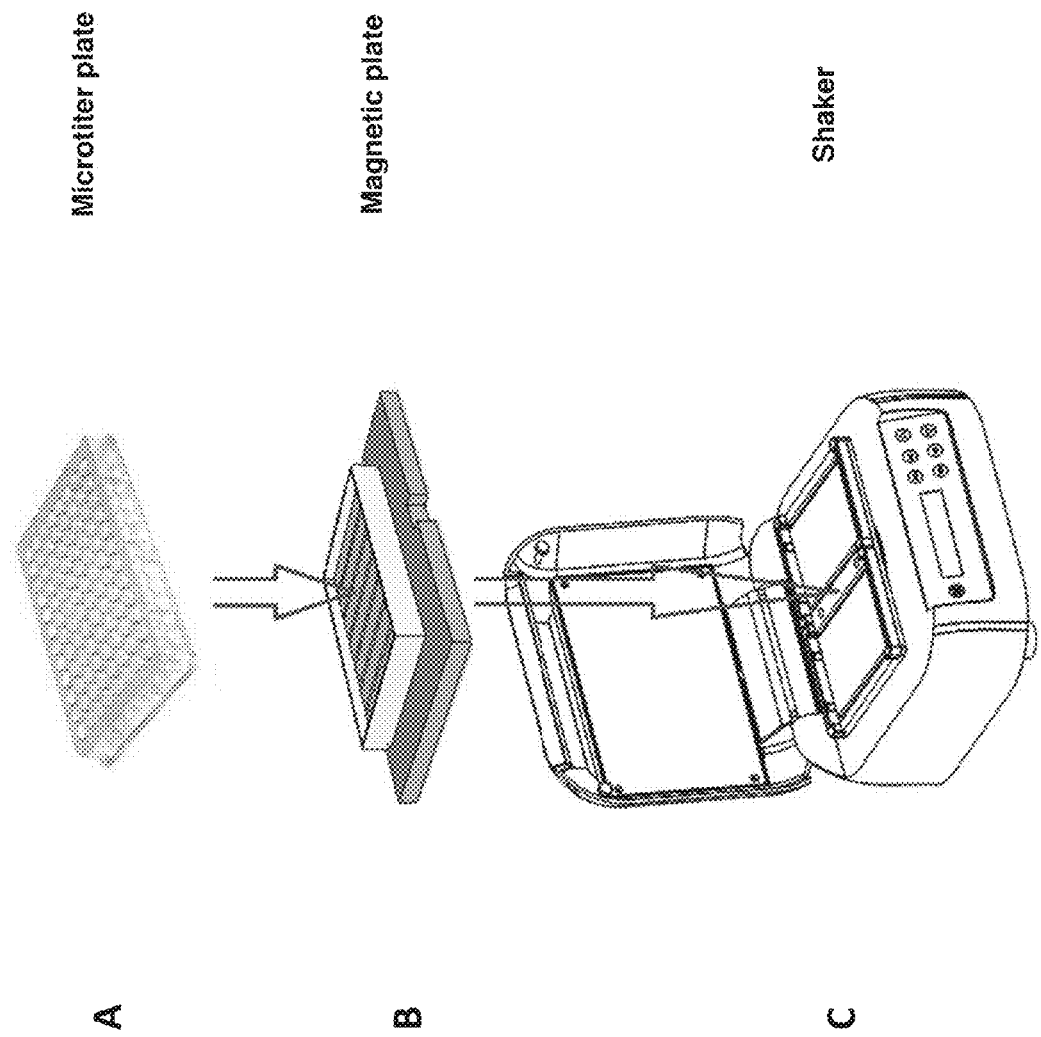
FIG. 13 illustrates an exemplary embodiment of a magnetic aggregating device containing a magnetic structure and a motor.

FIG. 13 is an exemplary embodiment of a magnetic aggregating device containing a magnetic structure and a motor. As shown in FIG. 13B, the magnetic structure is a magnetic plate that is configured to hold the microtiter plate shown in FIG. 13A. The magnetic plate holding the microtiter plate can be placed into the shaker as shown in FIG. 13C such that the magnetic plate is brought into operable connection with the motor. The shaker contains the motor that, when in operation, causes the magnetic plate and the microtiter plate to move together when the magnetic plate is holding a microtiter plate. As can be seen in FIG. 13, the magnetic plate may be uncoupled from the shaker containing the motor. Note that other coupling configurations are also possible. Further note that the magnetic aggregating device may contain features in addition to a magnetic structure and a motor.

Magnetic Structures

A magnetic structure of the present disclosure is an apparatus configured to hold or contain one or more magnets such as, for example, exemplary magnetic plate 100 shown in FIG. 1A. The magnetic structure contains a number of magnets. The magnets may be composed of any magnetic material known in the art. For example, the magnets may be ferromagnets that are composed of ferrite, which exhibits a strong magnetic field. As shown in FIG. 1A, exemplary magnetic plate 100 contains six magnets, each magnet having a north pole and a south pole. The magnetic structure may contain more than six magnets or fewer than six magnets. A magnetic structure may contain, for example, two, three, four, five, six, seven, eight, nine, ten, eleven, or twelve or more magnets. Any number of magnets may be used so long as magnetic beads in all wells of the microtiter plate are capable of being influenced by a magnetic force generated by the magnetic structure. In an exemplary embodiment, a first magnet and a second magnet in the magnetic structure are oriented such that the first pole of the first magnet faces the first pole of the second magnet, the first magnet adjacent to the second magnet in the magnetic structure (FIGS. 1A and 1B). Additional structural arrangements of magnetic poles of magnets in the magnetic structure will be apparent to those skilled in the art and may find use herein. Note that magnetic plate 100 is merely exemplary and that other magnetic structures may be used herein. For example, FIG. 15 illustrates various views of an additional exemplary embodiment of a magnetic structure.

Each of the magnets in a magnetic structure of the disclosure may have a north pole and a south pole where each pole spans the longitudinal length of one side of the magnet. The magnets may be, for example, magnetic strips. Structurally, magnets may be, for example, circular, elliptical, rectangular, square, triangular, or any other structural shape known in the art.

The electromagnetic strength of the poles of the magnets in a magnetic structure may have, for example, a north (N) pole magnetic unit of about 2700±50 G (Gaussian units) and a south (S) pole magnetic unit of about 2600±50 G. The electromagnetic strength of a magnet in a magnetic structure of the present disclosure may be higher than about 2600 G or about 2700 G, or it may be lower than about 2600 G or about 2700 G. The electromagnetic strength of the magnet may be, for example about 2550 G to about 2600 G, about 2600 G to about 2650 G, about 2650 G to about 2700 G, or it may be about 2700 G to about 2750 G. One of skill in the art would readily recognize additional magnets of different magnetic strength that may be used herein. In some embodiments, the magnets have a magnetic strength that allows magnetic beads in a well of a microtiter plate to overcome the magnetic force and be suspended in solution at a high rotation speed described herein and is sufficient to aggregate a majority of the beads (e.g., at least about 80% of the beads in a well) at a low rotation speed described herein.

As is shown in the exemplary embodiment in FIG. 4, a microtiter plate sits on top of magnetic plate 100. Note that other magnetic structures configured to hold microtiter plates may also be used. Microtiter plates of the present disclosure may be, for example, standard 96-well microtiter plates used in in vitro assays that are well-known in the art. Exemplary microtiter plates may include, for example, those with a normal flat-bottom design or a conical multi-well microtiter plate. Examples may include the polystyrene 96-well microplates from Greiner Bio-One, 96-well microtiter plates from Thermo-Scientific, or the 96-well microtiter plates from Fisher.

The microtiter plate may be a microtiter plate that contains more than 96 wells or less than 96 wells. For example, a microtiter plate with 6 wells, with 12 wells, with 48 wells, or with more than 48 wells may be used. A microtiter plate with, for example, 384 wells, or with more than 384 wells may be used. A microtiter plate with between 6 wells and 1,000 wells may be used. Various microtiter plates with diverse numbers of wells are well known in the art. Various microtiter plates with various numbers of wells may be used herein as long as magnetic beads in all wells of the microtiter plate are capable of being influenced by a magnetic force generated by the magnetic structure.

Movement

Magnetic aggregating devices of the present disclosure may contain a motor. In FIG. 1A, the magnetic aggregating device contains a motor that is connected to magnetic plate 100. Additionally, an exemplary connection of a magnetic structure to a motor is further illustrated in FIG. 13. Note that the motor may be capable of connecting to other magnetic plates or other magnetic structures. The motor's connection to the magnetic plate may be direct or it may be indirect. Operation of the motor causes the magnetic plate to move rotationally. When a microtiter plate sits on top of the magnetic plate, operation of the motor causes the microtiter plate and the magnetic plate to move together in a rotational fashion. The movement produces a relative centrifugal force on the microtiter plate.

Various motors for controlling movement of a structure are known in the art and may be used in magnetic aggregating devices described herein. The motor may be a component of a shaker apparatus or a similar structure as long as the motor is capable of producing movement. The magnetic aggregating device may have a controller adapted to operate the motor. The controller may be configured to operate the motor at various speeds such as, for example, a low speed and a high speed. The motor may be configured to produce movement of the magnetic structure at multiple speeds. The motor may be configured, for example, to produce movement at two speeds, such as a first speed and a second speed. The movement speeds produced by the motor may be measured as rotations per minute, or "RPM". The movement produced by the motor may be produced by the action of a controller adapted to operate the motor or by any means of operation known in the art. Additionally, the motor may be configured to produce movement for a given duration such that the motor ceases to produce movement following expiration of a given duration of time. The duration of movement may be controlled, for example, by the controller adapted to operate the motor at various speeds, a similar controller, or manual control. Motors, controllers, and mechanisms of controlling aspects of movement, such as speed and duration, are well-known in the art and may be used in the magnetic aggregating devices described herein.

The movement produced as a result of the operation of the motor may be rotation, such that the magnetic structure moves in circular rotations with the plane of rotation parallel to the surface defined by the surface of the magnets. The movement may also be, for example, reciprocal, vertical, transverse, or any other type of movement known in the art as long as the movement is capable of producing a sufficient force that allows magnetic beads to be suspended in a well of a microtiter plate when moving at a high speed. The motor may be configured to produce two or more movements that may occur as combinations of any type of movement known in the art in a symmetrical or an asymmetrical fashion. One of skill in the art would recognize additional types of movement that may be exhibited by the magnetic structures described herein.

Various motors may have certain physical or other parameters associated with that particular motor. For example, various motors may have various movement speed ranges and heating capabilities. A table of exemplary physical parameters associated with an exemplary shaker containing a motor of an exemplary magnetic aggregating device is provided in FIG. 16. Note that other values associated with the parameters listed are also possible. Further note that other parameters not listed may also be present.

Aspirators

The magnetic aggregating device may include an aspirator configured to remove a portion of the content of a well of a microtiter plate from the well of the microtiter plate. Aspiration may involve the process of liquid suction from, for example, a well in a microtiter plate. The aspirator may be configured to remove liquid from all wells of a microtiter plate simultaneously. Any aspirator known in the art that is designed for liquid aspiration may be used herein. For example, the 96 Tube Aspiration Manifold (VP 177A-1) from V&P Scientific, Inc. may be used herein.

Methods for Magnetic Aggregation and Washing

Figure 5:
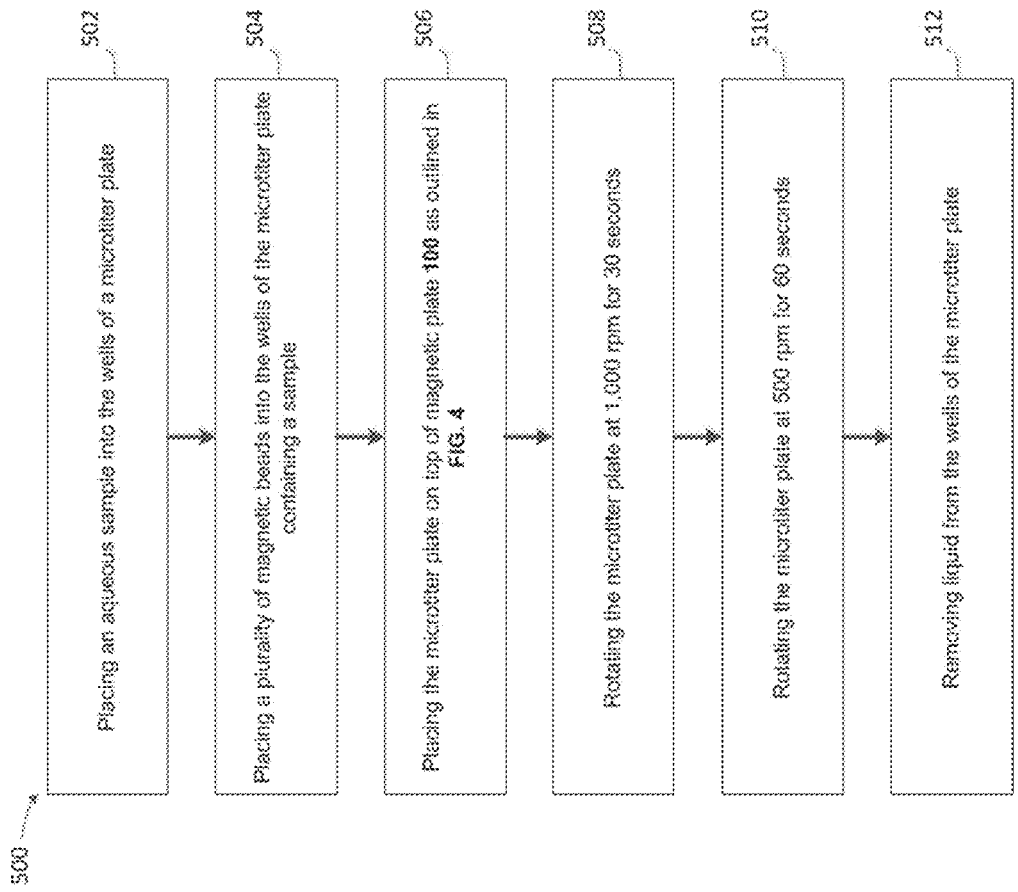
FIG. 5 illustrates an exemplary embodiment of a magnetic aggregating and washing process.

FIG. 5 depicts exemplary process 500 for aggregating and washing molecules in a sample. In step 502, an aqueous sample is placed into the wells of a microtiter plate. The sample contains one or more molecules of interest that are to be isolated and/or detected. In step 504, magnetic beads are placed into the wells of the microtiter plate containing a sample. The magnetic beads are conjugated with or attached to an agent that specifically interacts with a molecule in the sample.

In step 506, the microtiter plate is placed on top of a magnetic plate, such as magnetic plate 100 (FIG. 1A).

In step 508, the microtiter plate is rotated at 1,000 RPM for 30 seconds. During step 508, the magnetic beads in the wells are distributed throughout the well in the microtiter plate. Distribution of the magnetic beads occurs as the rotation produces a relative centrifugal force that exceeds the magnetic force between the magnetic beads and the magnetic plate. In step 510, the microtiter plate is rotated at 500 RPM for 60 seconds. During step 510, a majority of the magnetic beads in a well in the microtiter plate aggregate to a specific portion of that well in the plate. Aggregation of the magnetic beads occurs as the rotation produces a relative centrifugal force that does not exceed the magnetic force between the magnetic beads and the magnetic plate.

In step 512, liquid is removed from the wells of the microtiter plate. The liquid is substantially depleted of the one or more molecules that the magnetic beads were designed to isolate. The remaining contents of the wells of the microtiter plate are magnetic beads in association with one or more molecules of interest that were present in the original processed aqueous sample.

Samples

The microtiter plate contains a well containing a sample. A sample may include, for example, a composition containing a material, such as a molecule, to be isolated. The sample may be a biological sample (i.e., any material obtained from a living source (e.g. human, animal, plant, bacteria, fungi, protist, virus)). The biological sample can be in various forms including solid materials (e.g. tissue, cell pellets, swabs, cell culture media, and biopsies) and biological fluids (e.g. urine, blood or fractions of whole blood such as plasma, cerebrospinal fluid, tissue fluids or homogenates, saliva, amniotic fluid and mouth wash (containing buccal cells)). Solid materials typically are mixed with a liquid to produce a substantially aqueous solution.

Samples may include an environmental sample such as a sample from water, air, soil, or from any other environmental source. Samples may include, for example, man-made compositions for which a particular molecule of interest is to be isolated. Examples may include the products of a polymerase chain reaction (PCR) or the products of other biochemical reactions.

The samples may contain a biomolecule. A biomolecule may be, for example, a material derived from a living source. Such samples may include biomolecules and biopolymers. A biomolecule may also be any molecule that is produced by a living organism such as, for example, large polymeric molecules such as proteins, polysaccharides, lipids, and nucleic acids as well as small molecules such as, for example, primary metabolites, secondary metabolites, and natural products.

The sample may also contain, for example, an analyte. An analyte may include, for example, proteins in the form of native proteins as they are translated in the cell and proteins having post-translational translocation, processing, modifications, and the like. Protein analytes may be truncated after translation, or for example may be phosphorylated, or have other modifications such as to the backbone or to the side chain of any amino acid residue. An analyte may also include metabolic derivatives of such proteins as well as complexes, whether active or not, of one or more proteins with one or more other substituents found in a cell. An analyte may also include, for example, a DNA molecule, a DNA-analog-molecule, an RNA-molecule, an RNA-analog-molecule, an amino acid, a nucleotide, a protein, an enzyme, a lipid, a phospholipid, a carbohydrate moiety, a polysaccharide, an antigen, a virus, a cell, an antibody, a small molecule chemical compound, or an antibody fragment.

The sample may also include, for example, a chemical compound. A chemical compound may include, for example, any chemical substance containing two or more different chemical elements with a unique and defined chemical structure.

Magnetic Beads

The microtiter plate contains a well containing a number of magnetic beads. The magnetic beads may be composed of a polymeric material with each magnetic bead being substantially identical in shape and size. The magnetic beads may be composed of a paramagnetic material or a ferromagnetic material that results in the attraction of the magnetic beads to a magnet when an external magnetic field is present in the vicinity of the magnetic beads. Suitable ferromagnetic materials may include, for example, iron, nickel, cobalt, and alloys of rare earth metals.

Magnetic beads of the present disclosure may possess any geometric shape so long as they are capable of being placed into a well of a microtiter plate. The magnetic beads may be spherical, including semi-spherical, in shape. The magnetic beads may be ovoid in shape. The magnetic beads may be cubical in shape including, for example, rectified cubes, rectangular cubes, truncated cubes, cantellated cubes, omnitruncated cubes, or snub cubes. The magnetic beads may be cylindrical in shape including, for example, right circular cylinders, elliptic cylinders, or oblique cylinders. The magnetic beads may be conic in shape including, for example, right circular cones or oblique circular cones. The magnetic beads may be pyramidal in shape including, for example, square pyramids or pentagonal pyramids. The magnetic beads may be tetrahedral in shape. The magnetic beads may be prismic in shape. Additionally, the magnetic beads may be any form of polyhedron including, for example, dodecahedrons, icosidodecahedrons, rhombic triacontahedrons, or rhombic dodecahedrons. The magnetic beads may have a variety of dimensions, including for example substantially flattened, so long as they are capable of being placed into a well of a microtiter plate.

A magnetic bead of the present disclosure may measure no more than about 1 mm, about 750 µm, about 500 µm, about 400 µm, about 300 µm, about 250 µm, about 200 µm, about 175 µm, about 150 µm, about 125 µm, about 100 µm, about 90 µm, about 80 µm, about 70 µm, about 60 µm, about 50 µm, about 40 µm, about 30 µm, about 20 µm, or about 10 µm at its widest dimension, inclusive, including every value in between these numbers. The magnetic beads may have a variety of other dimensional properties, including for example substantially flattened shapes, so long as they are capable of being placed into a well of a microtiter plate.

A well of a microtiter plate may include more than 2, more than 20, more than 30, more than 40, more than 50, more than 60, more than 70, more than 80, more than 90, or more than 100 magnetic beads, inclusive, as well as any numerical value in between these numbers. A well of a microtiter plate may include more than $10^2$, more than $10^3$, more than $10^4$, more than $10^5$, more than $10^6$, more than $10^7$, more than $10^8$, more than $10^9$, more than $10^{10}$, more than $10^{11}$, or more than $10^{12}$ magnetic beads, inclusive, as well as any numerical value in between these numbers. A well of a microtiter plate may include or contain between about 300 magnetic beads and about 2,500 magnetic beads.

The magnetic beads may have an agent immobilized to their surface such that the agent can specifically bind a molecule present in a sample. The agent may be, for example, an antibody or an antibody fragment that specifically binds a protein, protein fragment, peptide, or any other molecule or compound capable of specifically interacting with the antibody or antibody fragment. The agent may be, for example, a single-stranded nucleic acid, such as an ssDNA or an ssRNA, capable of hybridizing to a specific nucleotide sequence of a nucleic acid. The agent may be, for example, an immobilized ligand capable of specifically interacting with a molecule or compound present in a sample Other agents that can be immobilized onto the surface of a magnetic bead to specifically bind a molecule of interest are well-known in the art.

One of skill in the art would readily recognize that many types and varieties of magnetic beads are commercially available or may be custom designed and may be used herein.

Speeds and Durations

Microtiter plates sitting on top of magnetic structures of the present disclosure are rotated at certain speeds for certain durations of time. For example, rotation of the microtiter plate at a first speed for a first duration may act to distribute a majority of the magnetic beads in the wells of the microtiter plate throughout a given well. This is illustrated in a graphical depiction seen in FIG. 10A. In this instance, the centrifugal force produced by the first speed for the first duration exceeds the magnetic force between the magnetic beads in wells of the microtiter plate and the magnetic plate. Additionally, rotation of the microtiter plate at a second speed for a second duration may act to aggregate a majority of the magnetic beads in a well at a specific portion of that well. This is illustrated in a graphical depiction seen in FIG. 14. In this instance, the centrifugal force produced does not exceed the magnetic force between the magnetic beads and the magnetic plate and facilitates magnetic bead aggregation.

The first speed may be, for example, a speed that is a high speed or that produces a high-speed rotation. The first speed may be about 800 RPM to about 850 RPM, about 850 RPM to about 900 RPM, about 900 RPM to about 950 RPM, about 950 RPM to about 1,000 RPM, about 1,000 RPM to about 1,050 RPM, about 1,050 RPM to about 1,100 RPM, about 1,100 RPM to about 1,150 RPM, about 1,150 RPM to about 1,200 RPM, about 1,200 to about 1,250 RPM, or about 1,250 RPM to about 1,300 RPM or higher. The first speed may be about 800 RPM to about 900 RPM, about 900 RPM to about 1,000 RPM, about 1,000 RPM to about 1,100 RPM, about 1,100 RPM to about 1,200 RPM, or about 1,200 RPM to about 1,300 RPM or higher. The first speed may be about 800 RPM to about 1,250 RPM. The first speed may be about 1,000 RPM.

The first duration may be, for example, a duration of time at a first speed sufficient to distribute a majority of the magnetic beads in a well of the microtiter plate throughout the well of the microtiter plate. The first duration may be about 15 seconds to about 25 seconds, about 25 seconds to about 35 seconds, about 35 seconds to about 45 seconds, about 45 seconds to about 55 seconds, or about 55 seconds to about 65 seconds or longer. The first duration may be about one minute to about two minutes, about two minutes to about three minutes, or about three minutes or longer. The first duration may be about 20 seconds to about 40 seconds. The first duration may be about 30 seconds. The first duration may be about 60 seconds.

Rotation of the microtiter plate at the first speed produces a relative centrifugal force, or "RCF," that exceeds the magnetic force between the magnetic beads in a well of the microtiter plate and the magnetic structure. An equation for calculating RCF is provided in EQ. 1, $$RCF=1.118\times10^{-5}\times R\times 2RPM \qquad (EQ.\ 1)$$

where "R" is the rotating radius of the magnetic structure, and "RPM" is rotations per minute.

The second speed may be, for example, a speed that is a low speed or that produces a low-speed rotation. The first speed may be about 200 RPM to about 250 RPM, about 250 RPM to about 300 RPM, about 300 RPM to about 350 RPM, about 350 RPM to about 400 RPM, about 400 RPM to about 450 RPM, about 450 RPM to about 500 RPM, about 500 RPM to about 550 RPM, about 550 RPM to about 600 RPM, or about 600 RPM to about 650 RPM. The second speed may be about 300 RPM to about 400 RPM, about 400 RPM to about 500 RPM, or about 500 RPM to about 600 RPM. The second speed may be about 400 RPM to about 600 RPM. The second speed may be about 500 RPM.

The second duration may be, for example, a duration of time at a second speed sufficient to aggregate a majority of the magnetic beads in a well at a portion of that well. The second duration may be about 45 seconds to about 50 seconds, about 50 seconds to about 55 seconds, about 55 seconds to about 60 seconds, about 60 seconds to about 65 seconds, or about 65 seconds to about 70 seconds, or about 70 seconds to about 75 seconds or longer. The second duration may be about one minute to about two minutes, about two minutes to about three minutes, or about three minutes or longer. The second duration may be about 50 seconds to about 70 seconds. The second duration may be about 60 seconds.

Rotation of the microtiter plate at the second speed produces a relative centrifugal force, or "RCF," that does not exceed the magnetic force between the magnetic beads in a well of the microtiter plate and the magnetic structure, which facilitates magnetic bead aggregation at a portion of the well. In the absence of rotation, the magnetic beads in a well of the microtiter plate may collapse, in a non-aggregate fashion, to the bottom of the wells in the presence of a magnetic force from the magnetic structure.

Liquid Removal from Wells

Exemplary process 500 may involve removing a portion of the contents in a well of the microtiter plate from the well of the microtiter plate following rotating the microtiter plate at the second speed for a second duration. Following the second speed at the second duration, the magnetic beads in a well are aggregated at a specific portion of that well. The contents that are removed may include, for example, the portion of the sample that does not contain magnetically aggregated magnetic beads. Such contents may include, for example, an aqueous portion of the sample that is substantially depleted of a molecule that has bound to the magnetic beads.

Removal of the contents in a well of the microtiter plate may be done manually. Alternatively, removal of the contents may be accomplished with an aspirator. Methods of liquid removal and aspiration of liquid from a well of a microtiter plate are well known in the art and are described herein. The removed contents may be disposed of or they may be subjected to further rounds of magnetic aggregation and washing. Similarly, the aggregated magnetic beads remaining in a well of the microtiter plate may be subjected to further rounds of magnetic aggregation and washing.

Magnetic Bead Recovery

Exemplary process 500 may involve a quantitative assessment of the number of aggregated magnetic beads present in a well of the microtiter plate following liquid removal from that well after a round of magnetic aggregation and washing. This assessment may be based on the number of magnetic beads remaining in a well after a given number of rounds of magnetic aggregation, washing, and liquid removal from that well in comparison to the total number of beads that were originally placed into that well prior to magnetic aggregation, washing, and liquid removal, which can be represented as a percentage (%) of recovery of the magnetic beads, or percent (%) recovery yield. The number of rounds of magnetic aggregation may be, for example, one round, two rounds, three rounds, four rounds, five rounds, six rounds, or more than six rounds. After a given number of rounds of magnetic bead aggregation, washing, and liquid removal, the percent recovery yield of the magnetic beads in a well of a microtiter plate may be, for example, in the range of about 50% to about 55%, about 55% to about 60%, about 60% to about 65%, about 65% to about 70%, about 70% to about 75%, about 75% to about 80%, or more than about 80% bead recovery yield. After six rounds of magnetic aggregation, washing, and liquid removal, about 80% of the original input magnetic beads in a well of a microtiter plate may be recovered.

EXAMPLES

To better facilitate an understanding of the embodiments of the disclosure, the following examples are presented. The following examples are merely illustrative and are not meant to limit any embodiments of the present disclosure in any way.

Example 1

Low-Speed Magnetic Aggregation of Magnetic Beads

Example 1 demonstrates that low-speed rotation of magnetic beads in a well of a microtiter plate rotating on a magnetic plate functions to aggregate the magnetic beads in a well at a specific portion of that well in the microtiter plate. Following rotation, magnetic beads in the wells of the microtiter plate become aggregated, meaning that in an exemplary well the beads in that well are aggregated at a specific portion of the well.

Materials and Methods

Standard 96-well microtiter plates were selected and each well was supplied with a given amount of magnetic beads. Two plates were used: one plate containing 300 magnetic beads and the other plate containing 2,500 magnetic beads. The magnetic beads were suspended in an aqueous solution in the wells. Microtiter plates with wells housing the magnetic beads were placed on top of a magnetic plate as outlined in FIG. 1A in a magnetic aggregating device as outlined in FIG. 13. Various RPM speeds were assayed to determine how the given speed impacts the arrangement of the magnetic beads in the wells. Plates were rotated at a given speed for 60 seconds. Following rotation at a given speed, wells were selected from diverse regions of the microtiter plate and imaged to analyze magnetic bead distribution in the wells.

Results

Based on analysis of the microtiter plate wells following rotation, it was found that low-speed rotation of the microtiter plate on the magnetic plate is capable of aggregating magnetic beads in a well to a specific portion of that well in the microtiter plate.

Figure 6:
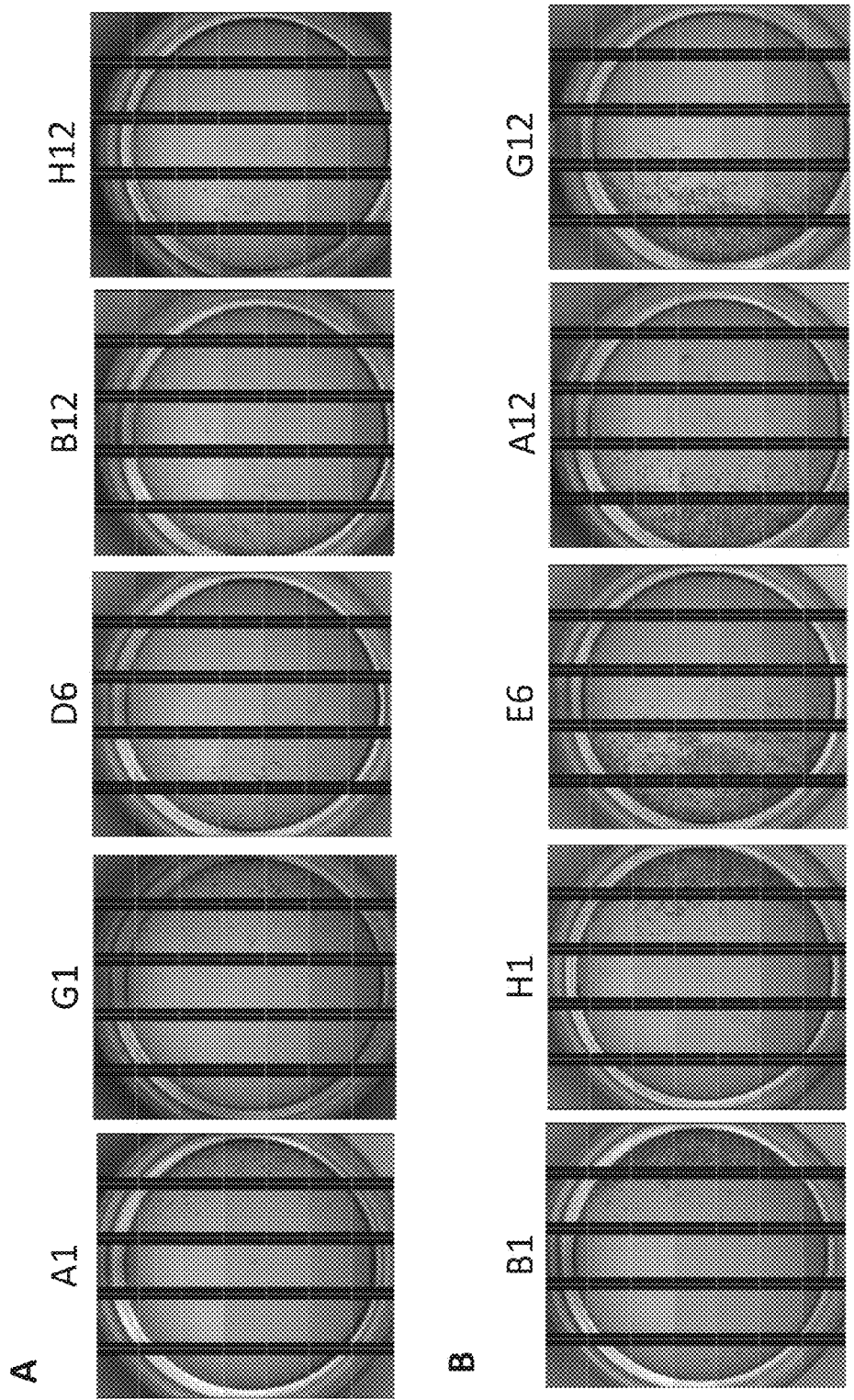
FIG. 6A illustrates the distribution of 300 magnetic beads inside selected wells of a microtiter plate following rotation of the microtiter plate at 300 RPM (rotations per minute) for 60 seconds on a magnetic plate.
FIG. 6B illustrates the distribution of 2,500 magnetic beads inside selected wells of a microtiter plate following rotation of the microtiter plate at 300 RPM for 60 seconds on a magnetic plate. Various wells from different regions of the microtiter plates following rotation are presented in standard letter-number plate well-labeling format (see e.g.

As can be seen in the wells supplied with 300 magnetic beads in FIG. 6A, rotation at 300 RPM resulted in aggregation of magnetic beads in a well to specific portions of that well. The portion of a well in which the magnetic beads aggregated in that well was not uniform across the various wells of the microtiter plate. For example, wells "A1" and "G1" aggregated magnetic beads in a portion opposite to the location of the magnetic bead aggregates observed in wells "D6," "B12," and "H12." Similar magnetic bead aggregation results were observed in wells supplied with 2,500 magnetic beads (FIG. 6B).

Figure 7:
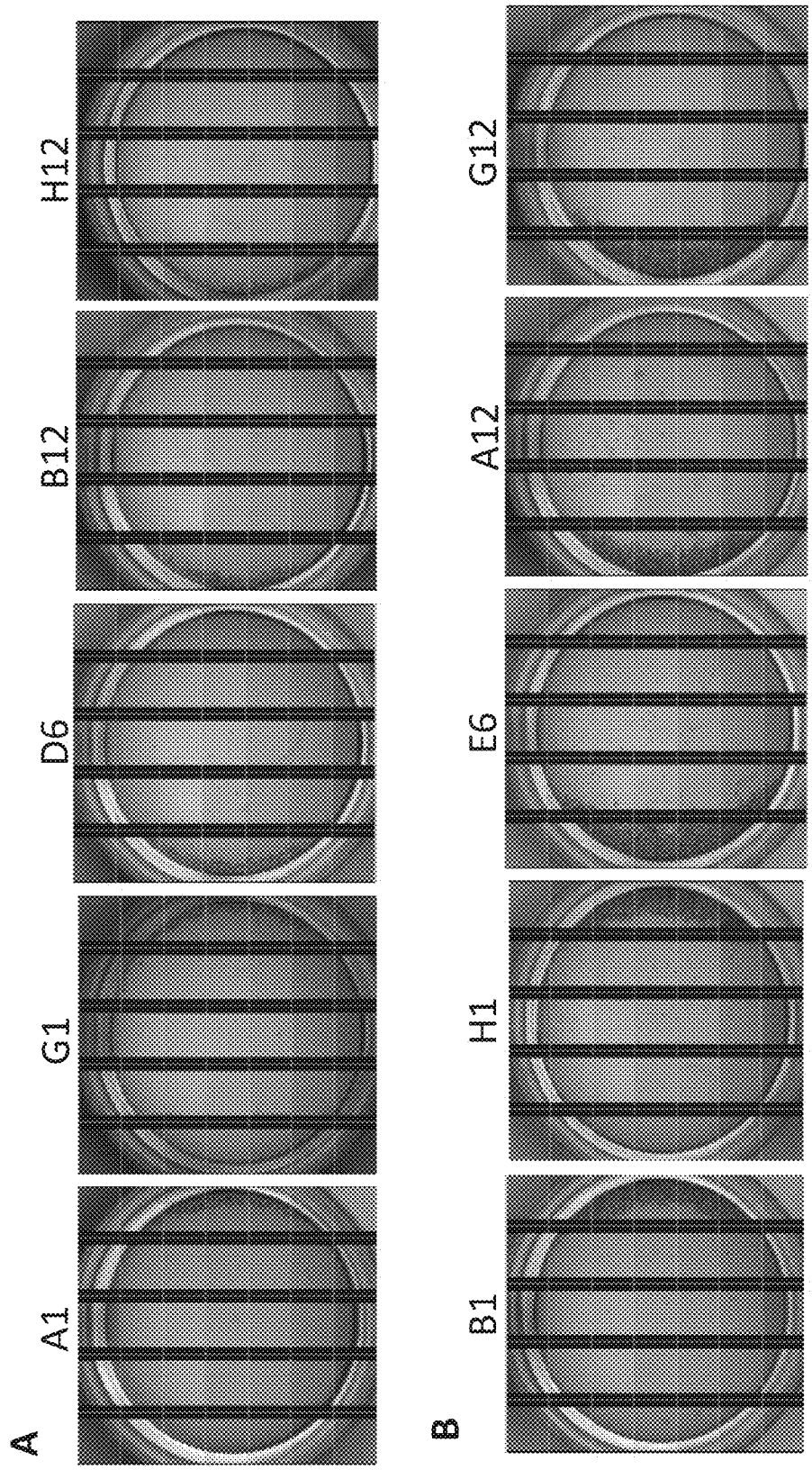
FIG. 7A illustrates the distribution of 300 magnetic beads inside selected wells of a microtiter plate following rotation of the microtiter plate at 500 RPM for 60 seconds on a magnetic plate.
FIG. 7B illustrates the distribution of 2,500 magnetic beads inside selected wells of a microtiter plate following rotation of the microtiter plate at 500 RPM for 60 seconds on a magnetic plate.
Figure 8:
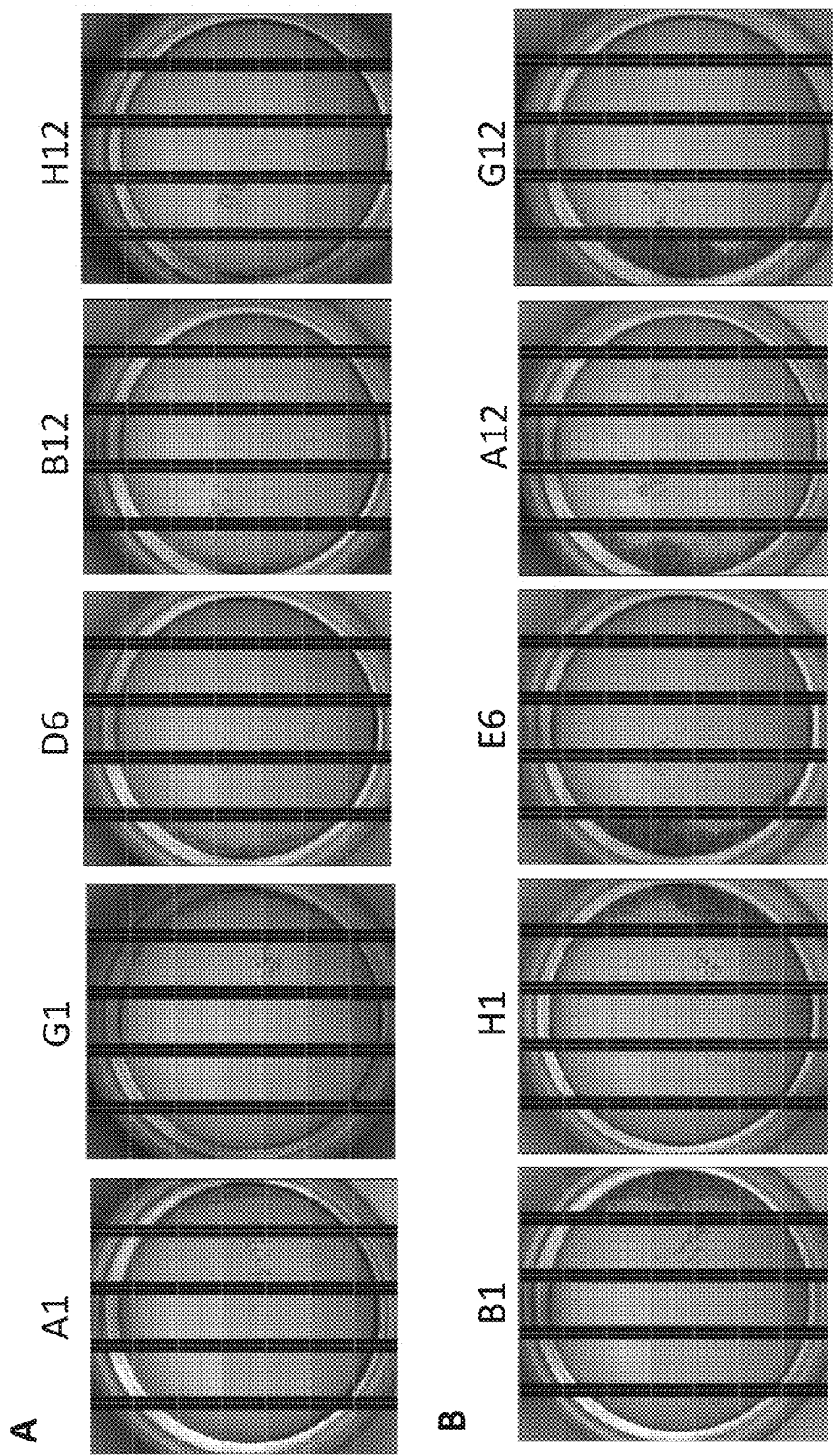
FIG. 8A illustrates the distribution of 300 magnetic beads inside selected wells of a microtiter plate following rotation of the microtiter plate at 600 RPM for 60 seconds on a magnetic plate.
FIG. 8B illustrates the distribution of 2,500 magnetic beads inside selected wells of a microtiter plate following rotation of the microtiter plate at 600 RPM for 60 seconds on a magnetic plate.

Although 300 RPM was sufficient to result in magnetic bead aggregation in a well to a specific portion of that well, even tighter magnetic bead aggregates were formed at 500 RPM (FIG. 7) and 600 RPM (FIG. 8). This was observed for wells supplied with both 300 and 2,500 magnetic beads. Tight magnetic bead aggregates in a well formed at a specific portion of that well following plate rotation at 500 RPM. Similar results were also observed following rotation at 600 RPM, although 500 RPM appeared to produce the tightest magnetic bead aggregates.

Figure 9:
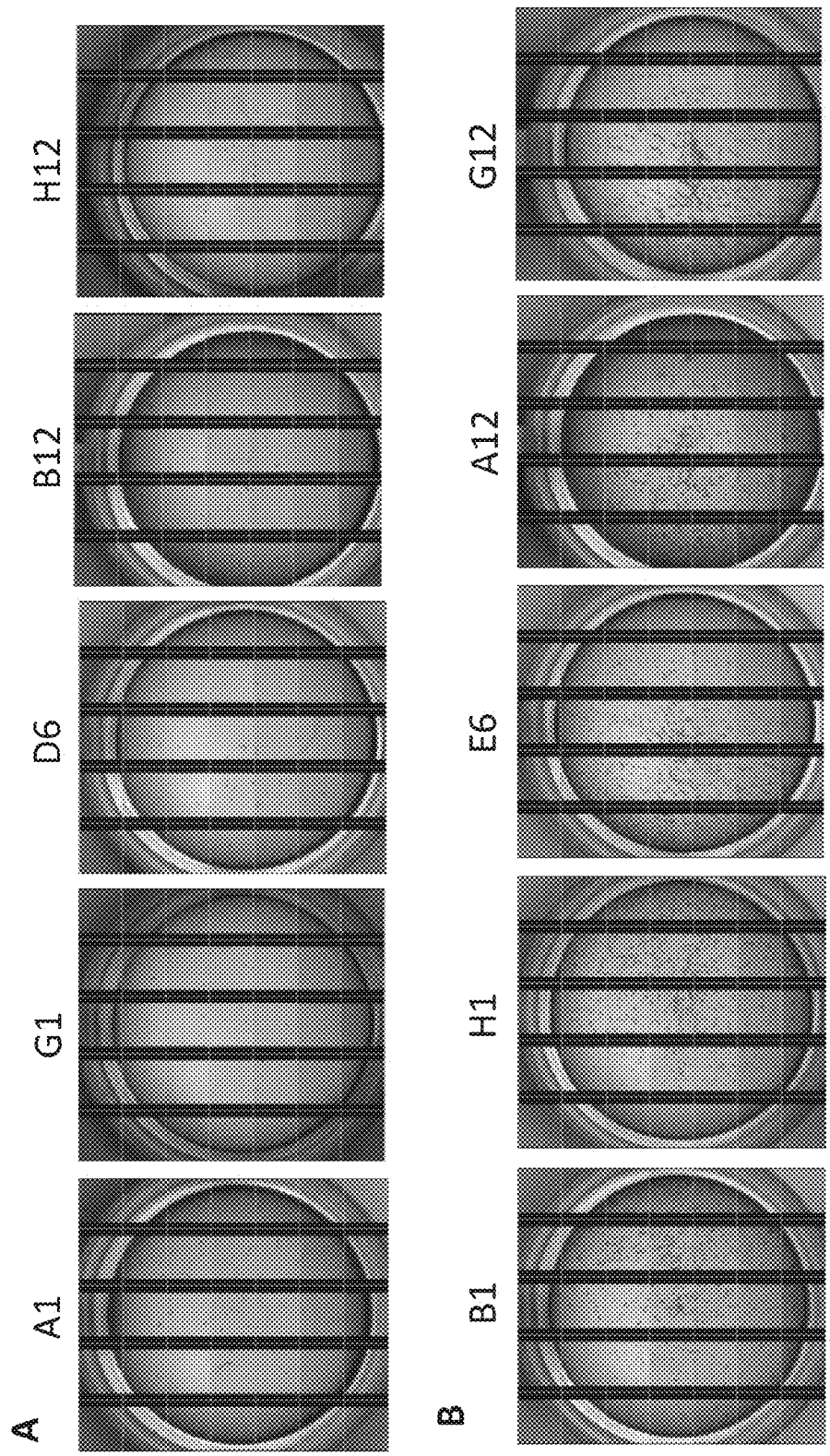
FIG. 9A illustrates the distribution of 300 magnetic beads inside selected wells of a microtiter plate following rotation of the microtiter plate at 800 RPM for 60 seconds on a magnetic plate.
FIG. 9B illustrates the distribution of 2,500 magnetic beads inside selected wells of a microtiter plate following rotation of the microtiter plate at 800 RPM for 60 seconds on a magnetic plate.

In contrast to the magnetic bead aggregation observed at rotation speeds of 300, 500, and 600 RPM, rotation at 800 RPM did not result in magnetic bead aggregation in a well at a specific portion of that well. As can be seen in FIG. 9, both 300 magnetic bead-containing wells and 2,500 magnetic bead-containing wells exhibited scattered magnetic bead distribution. There was still a tendency for left or right-side magnetic bead location preference depending on the location of the well on the microtiter plate as described above. Regardless, 800 RPM was not a sufficiently low-speed rotation to induce magnetic aggregation of the magnetic beads in a well to a specific portion of that well in a microtiter plate.

Example 2

Impact of High-Speed Rotation on Magnetic Bead Distribution

Example 2 demonstrates that magnetic beads in a well of a microtiter plate are distributed throughout that well using high-speed rotation either on a magnetic plate or on a non-magnetic plate.

Materials and Methods

Standard 96-well microtiter plates were selected and wells were supplied with magnetic beads. The magnetic beads were suspended in an aqueous solution in the wells. Microtiter plates with wells housing the magnetic beads were placed either on top of a magnetic plate as outlined in FIG. 1A in a magnetic aggregating device as outlined in FIG. 13, or placed on top of a non-magnetic shaker, which is similar to the magnetic aggregating device but with a non-magnetic plate holding the microtiter plate. A rotation speed of 1,000 RPM was assayed to determine the impact of high-speed rotation on magnetic bead aggregation in the wells of each plate. Microtiter plates were rotated on their respective device at 1,000 RPM for 60 seconds. Following rotation, wells were imaged to analyze magnetic bead distribution.

Results

Figure 10:
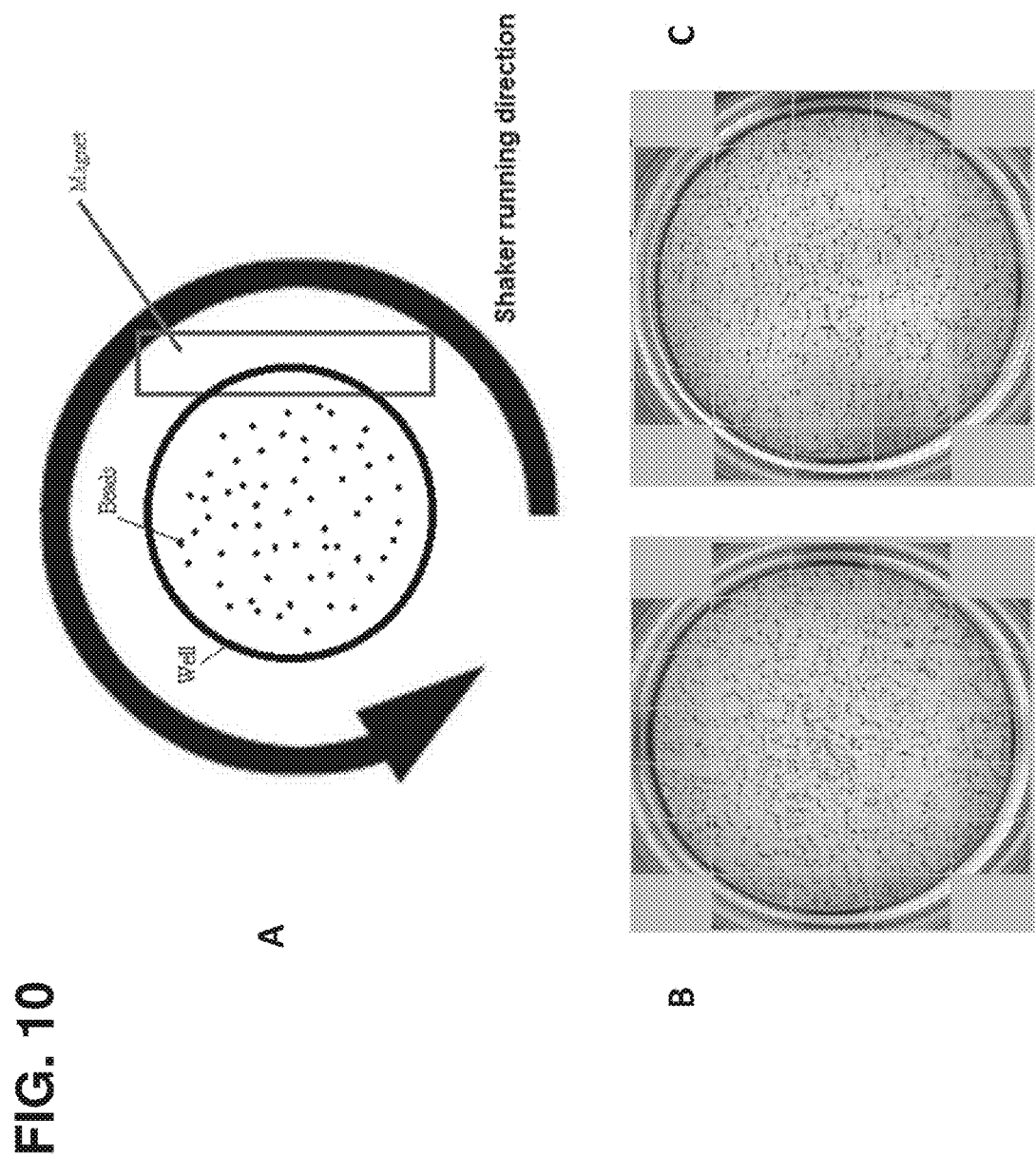
FIG. 10A illustrates a graphical depiction of the distribution of magnetic beads inside a well of a microtiter plate following rotation of the plate at a high-speed rotation in a magnetic aggregating device.
FIG. 10B illustrates the distribution of magnetic beads inside a representative well of a microtiter plate following rotation of the plate at 1,000 RPM for 60 seconds on a non-magnetic shaker.
FIG. 10C illustrates the distribution of magnetic beads inside a representative well of a microtiter plate following rotation of the plate at 1,000 RPM for 60 seconds on a magnetic aggregating device.

From Example 1, it was found that low-speed rotation of a microtiter plate rotating on a magnetic plate was capable of magnetically aggregating magnetic beads in a well at a specific region of that well in the microtiter plate. In contrast to low-speed rotations, it was found that high-speed rotations (1,000 RPM) were capable of distributing the magnetic beads throughout the well (FIG. 10). Magnetic bead distribution was observed in the wells of the microtiter plates following high-speed rotation either on a magnetic aggregating device or on a non-magnetic shaker (FIG. 10). This result suggests that the exertion of a magnetic force on the magnetic beads does not impact the ability of a high-speed rotation to distribute the magnetic beads in a well throughout that well. The speed of 1,000 RPM was sufficient to produce a relative centrifugal force to overcome the magnetic force between the magnetic plate and the magnetic beads and facilitates the distribution of magnetic beads in a well throughout that well.

Example 3

Washing Procedures

Example 3 demonstrates that efficient washing of magnetic beads in a well in a microtiter plate is achieved using high-speed rotation either on a magnetic plate or on a non-magnetic plate.

Materials and Methods

Standard 96-well microtiter plates were selected and wells were supplied with magnetic beads. The magnetic beads were suspended in a fluorescent aqueous solution in the wells. Microtiter plates with wells housing the magnetic beads suspended in the fluorescent solution were either placed on top of a magnetic plate as outlined in FIG. 1A in a magnetic aggregating device as outlined in FIG. 13, or placed on top of a non-magnetic shaker.

Figure 11:
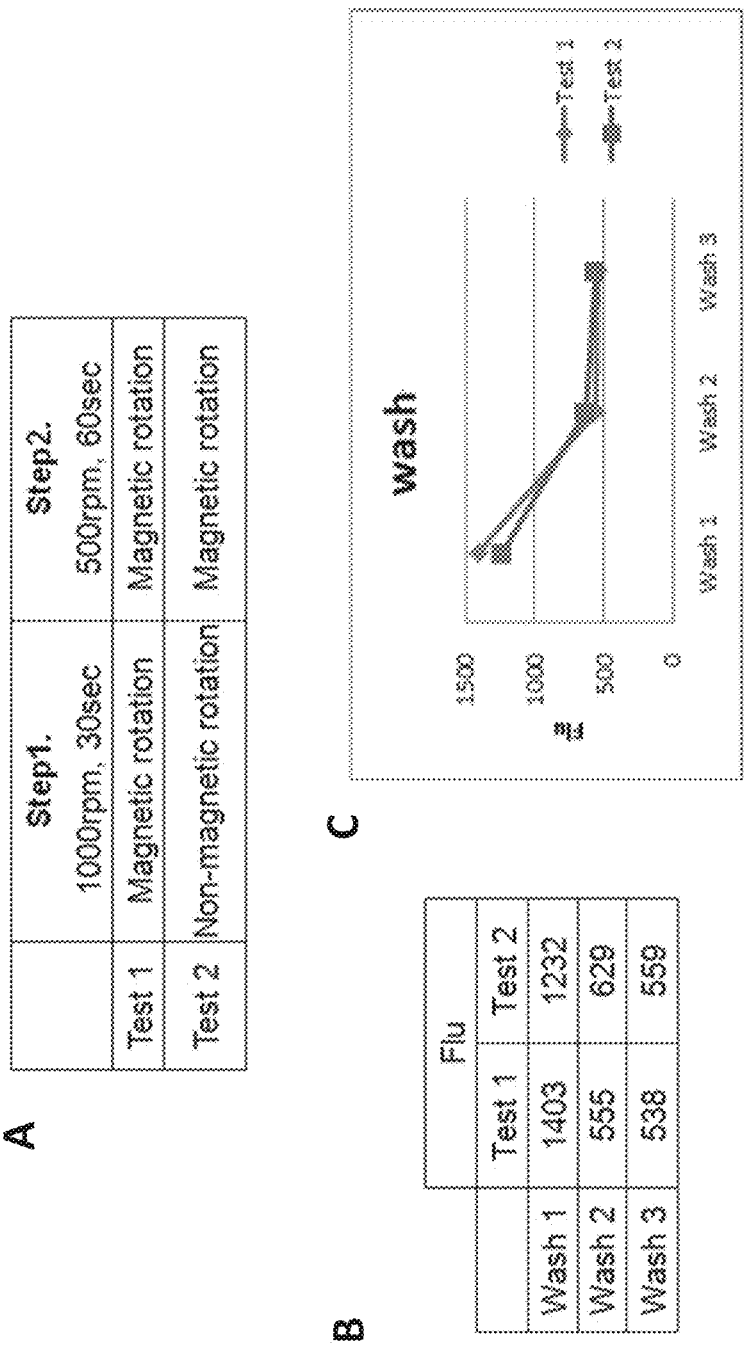
FIG. 11A illustrates the various steps in magnetic bead test washing schemes involving washing away of a fluorescent solution from a magnetic bead in a well of a microtiter plate.
FIG. 11B illustrates the results of the various test wash schemes in terms of fluorescence remaining following magnetic bead washing.
FIG. 11C illustrates a graphical depiction of the results from FIG. 11B. "Flu"=fluorescence units; a quantitative measure of fluorescence intensity.

A magnetic bead washing procedure was employed having two steps, but with two different test procedures (see FIG. 11A). In the first step (Step 1), microtiter plates were rotated at 1,000 RPM for 30 seconds on either a magnetic aggregating device (Test 1) or on a non-magnetic shaker (Test 2). Following the high-speed rotation at 1,000 RPM, the second step (Step 2) began where both microtiter plates were rotated at a low-speed rotation of 500 RPM for 60 seconds on the magnetic aggregating device (Test 1 and Test 2). The low-speed rotation in Step 2 served to aggregate the magnetic beads in a well to a specific portion of that well so that the liquid could be aspirated off without significant magnetic bead loss. At the end of the washing procedure, the fluorescent solution was removed from the wells and replaced with a non-fluorescent solution. The fluorescent signal from the magnetic beads was then assayed as a read-out of the effectiveness of the wash procedure. The wash procedure and measurement of magnetic bead fluorescence was repeated two additional times for a total of three magnetic bead washes.

Results

From Example 2, it was found that high-speed rotation of a microtiter plate on a magnetic plate was able to distribute magnetic beads throughout a well on the plate in a fashion analogous to rotation on a non-magnetic plate. To determine if the magnetic plate influences the ability of high-speed rotation to assist in washing magnetic beads, a washing assay was performed with high-speed rotation either in the presence or absence of a magnetic plate. It was found that the washing assay involving high-speed rotation on the magnetic aggregating device was equally as effective as the washing assay on the non-magnetic shaker (FIGS. 11B and 11C). This result suggests that a magnetic plate has no significant impact on the ability of high-speed rotations to effectively wash magnetic beads. For both test procedures, ~60% of original fluorescence was lost following the first wash, indicating an effective wash. For both test procedures, the third wash had little impact on further removing fluorescence from the magnetic beads.

Example 4

Magnetic Aggregation Improves Magnetic Bead Recovery Yield

Example 4 demonstrates that magnetic aggregating devices produce high magnetic bead recovery yields.
Materials and Methods Standard 96-well microtiter plates were selected and wells were supplied with approximately 1,000 magnetic beads. The magnetic beads were suspended in a solution in the wells. Microtiter plates with wells housing the magnetic beads suspended in the solution were placed on top of a magnetic plate as outlined in FIG. 1A in a magnetic aggregating device as outlined in FIG. 13.

Figure 12:
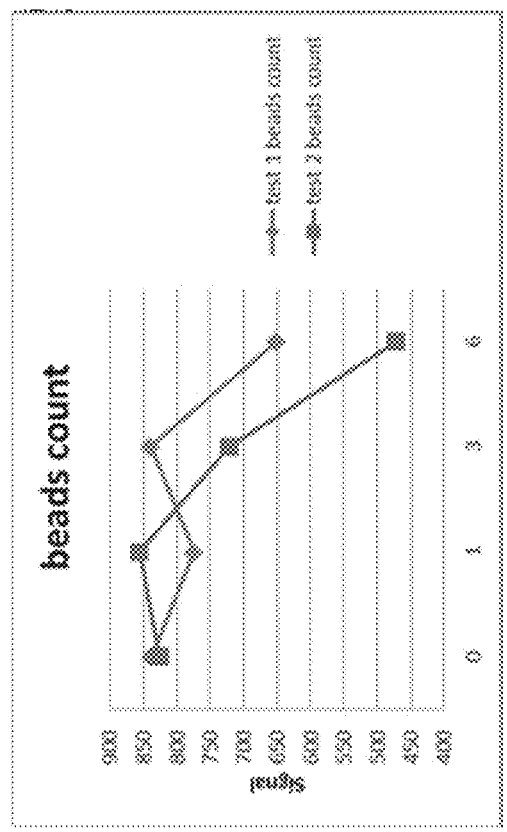
FIG. 12A illustrates the various steps in magnetic bead test washing schemes involving repeated magnetic bead washing and assessment of magnetic bead retention yield in a well of a microtiter plate following selected washes.
FIG. 12B illustrates the results of the various test washes in terms of starting magnetic beads and magnetic beads remaining after selected washes.
FIG. 12C illustrates a graphical depiction of the results from FIG. 12B. "Signal"=total number of magnetic beads counted after wash procedure.

A magnetic bead recovery assay following washing was employed having two steps, but with two different test procedures (see FIG. 12A). In the first step (Step 1), two microtiter plates were rotated at 1,000 RPM for 30 seconds on the magnetic aggregating device (Test 1 and Test 2). Following the high-speed rotation at 1,000 RPM, the second step (Step 2) began with rotating one of the microtiter plates at a low-speed rotation of 500 RPM for 60 seconds on the magnetic aggregating device (Test 1), whereas the other microtiter plate was allowed to sit on the magnetic aggregating device without any rotation (Test 2). At the end of the washing procedure, the solution was removed from the wells of both plates, the number of magnetic beads remaining in the well was assayed, and then new solution was added to the wells of both plates to re-initiate the washing procedure. The wash procedure and measurement of magnetic bead yield following solution removal after washing was repeated five additional times for a total of six magnetic bead washes. The number of magnetic beads present in the wells following the washing procedure was assayed after the first, third, and sixth washes.
Results To assay the effectiveness of a low-speed rotation on a magnetic plate on magnetic bead recovery in a magnetic bead washing assay, magnetic beads were washed either on a low-speed rotation on a magnetic plate or washed with no rotation on a magnetic plate (see FIG. 12A). After six washes using the washing regime outlined in Test 1 of FIG. 12A, ~78% of the input magnetic beads were recovered following the washing assay that involved a low-speed rotation of a microtiter plate on a magnetic plate. In contrast, only ~57% of the input magnetic beads were recovered following six washes using the washing assay that involved a microtiter plate sitting, as opposed to rotating, on a magnetic plate (FIGS. 12B and 12C). In the test where magnetic beads were washed by just sitting on the magnetic plate without rotation (Test 2), the magnetic beads in a well were distributed at the bottom of that well in the microtiter plate; no aggregation of the magnetic beads was observed. The results demonstrate that sample washing methods that include a low-speed rotation on a magnetic plate can improve magnetic bead recovery.
Conclusions As was seen in Example 4, sample washing methods using high-speed followed by low-speed rotation of a microtiter plate on a magnetic plate resulted in efficient magnetic bead recovery. Such methods also allow for efficient washing of the magnetic beads and thus the sample as a whole, as was seen in Example 3. Efficient washing is possible because the high-speed rotation of microtiter plates with wells housing magnetic beads allows the magnetic beads to become distributed throughout the wells in the plate, as was seen in Example 2. Distribution of the magnetic beads is an important aspect of a sample washing procedure, as this distribution increases the ability of each magnetic bead to be washed by having saturating contact with the wash solution. Subsequent low-speed rotation of the magnetic beads on a magnetic plate acts to aggregate the magnetic beads in a well of a microtiter plate to a specific portion of that well, as was seen in Example 1. This is efficient for liquid removal after washing, which allows for removal of the washing solution without significant loss of the magnetic beads.

Example 5

Magnetic Aggregation of Conjugated Magnetic Beads Delivers High Protein Yield

Example 5 demonstrates that magnetic aggregation and washing of antibody-conjugated magnetic beads incubated with a processed biological sample in wells of a microtiter plate delivers high protein yield from the processed biological sample.

Individual tissue samples are processed to extract cellular components using standard protocols for lysing cells. The processed tissues are further treated using standard cleaning and isolation protocols to remove a bulk of the cellular debris to yield substantially aqueous processed samples containing cellular biomolecules and other cellular content.

The processed samples are loaded into a standard microtiter plate, such as an ELISA plate. Each sample is loaded into a well of a 96-well microtiter plate. Approximately 2,500 conjugated magnetic beads are added to each well containing a processed sample in the microtiter plate. The magnetic beads are conjugated with an antibody that specifically recognizes a specific protein of interest that may be present in the processed samples.

The microtiter plate with wells containing the conjugated magnetic beads incubated with the processed samples is placed on top of a magnetic plate as outlined in FIG. 1A in a magnetic aggregating device. The microtiter plate is rotated at a speed of 1,000 RPM for 30 seconds on top of the magnetic plate. During the high-speed rotation, the conjugated magnetic beads are distributed throughout a well containing a processed sample. Following the high-speed rotation, the microtiter plate is rotated at a low-speed rotation of 500 RPM for 60 seconds. Following the low-speed rotation, conjugated magnetic beads in a well, which are conjugated to an antibody bound to a compatible protein, are aggregated to a specific portion on the boundary of that well in the microtiter plate. The liquid in the wells is then aspirated off to remove the sample portion not containing magnetic beads and a washing buffer is added to each well. As the antibody-conjugated magnetic beads bound to a compatible protein were aggregated to specific well exterior boundaries, magnetic bead loss during liquid aspiration is minimal. The high-speed and low-speed rotations as described above are repeated several times with washing buffer to remove residual molecules still remaining in the wells or interacting non-specifically with the magnetic beads.

Following the washing steps, a buffer is added to each well to disrupt the interaction between proteins and antibody-conjugated magnetic beads, releasing free protein into solution. The protein-containing solutions in each well are then assayed for protein content using standard protein detection methods. Standard calculations and methods are used to determine protein concentration in each sample. The protein concentrations obtained from the magnetic aggregating and washing method are significantly higher than those obtained with other protein isolation techniques. Thus, the magnetic aggregation and washing method demonstrates a useful method for high-throughput detection of proteins that delivers clean, high yields of protein.

What is claimed is:

1. A method for washing a sample in an assay, the method comprising:
   a) coupling a microtiter plate with a magnetic structure, wherein the microtiter plate sits on top of the magnetic structure,
      wherein the microtiter plate comprises a well comprising a sample and a plurality of magnetic beads,
      wherein the magnetic structure comprises a plurality of magnets each having a first pole and a second pole, the first pole and the second pole having opposite magnetic properties, and
      wherein a first magnet of the magnetic structure and a second magnet of the magnetic structure are oriented in the magnetic structure such that the first pole of the first magnet faces the first pole of the second magnet, the first magnet adjacent to the second magnet in the magnetic structure;
   b) rotating the microtiter plate such that the microtiter plate and the magnetic structure move together at a first speed for a first duration to distribute the plurality of magnetic beads in the well, wherein the rotation of the microtiter plate at the first speed produces a relative centrifugal force that exceeds the magnetic force between the magnetic beads in a well of the microtiter plate and the magnetic structure; and,
   c) rotating the microtiter plate such that the microtiter plate and the magnetic structure move together at a second speed for a second duration to aggregate a majority of the plurality of magnetic beads at a portion of the well, the second speed different from the first speed.

2. The method of claim 1, wherein the first speed is in the range of about 800 rotations per minute to about 1,250 rotations per minute.

3. The method of claim 1, wherein the first duration is in the range of about 20 seconds to about 40 seconds.

4. The method of claim 1, wherein the first speed is in the range of about 800 rotations per minute to about 1,250 rotations per minute and the first duration is in the range of about 20 seconds to about 40 seconds.

5. The method of claim 1, wherein the second speed is in the range of about 400 rotations per minute to about 600 rotations per minute.

6. The method of claim 1, wherein the second duration is in the range of about 50 seconds to about 70 seconds.

7. The method of claim 1, wherein the second speed is in the range of about 400 rotations per minute to about 600 rotations per minute and the second duration is in the range of about 50 seconds to about 70 seconds.

8. The method of claim 1, wherein the rotation of the microtiter plate at the second speed produces a relative centrifugal force that does not exceed the magnetic force between the magnetic beads in a well of the microtiter plate and the magnetic structure.

9. The method of claim 1, further comprising:
   removing a portion of the contents in the well of the microtiter plate from the well of the microtiter plate following rotating the microtiter plate at the second speed for the second duration.

10. The method of claim 9, wherein the portion of the well in which the majority of magnetic beads are aggregated is a first portion of the well, and wherein the contents are removed from a second portion of the well away from the first portion.

11. The method of claim 1, wherein the sample is a biological sample.

12. The method of claim 11, wherein the biological sample is a blood sample.

13. The method of claim 11, wherein the biological sample contains a nucleic acid or a protein.

14. The method of claim 1, wherein an agent that specifically binds to a nucleic acid or a protein in the sample is immobilized to the surface of a magnetic bead.

15. A method for washing a sample in an assay, the method comprising:
   a) coupling a microtiter plate with a magnetic structure, wherein the microtiter plate sits on top of the magnetic structure,
      wherein the microtiter plate comprises a well comprising a sample and a plurality of magnetic beads,
      wherein the magnetic structure comprises a plurality of magnets each having a first pole and a second pole, the first pole and the second pole having opposite magnetic properties, and
      wherein a first magnet of the magnetic structure and a second magnet of the magnetic structure are oriented in the magnetic structure such that the first pole of the first magnet faces the first pole of the second magnet, the first magnet adjacent to the second magnet in the magnetic structure;
   b) rotating the microtiter plate such that the microtiter plate and the magnetic structure move together at a first speed for a first duration to distribute the plurality of magnetic beads in the well; and,
   c) rotating the microtiter plate such that the microtiter plate and the magnetic structure move together at a second speed for a second duration to aggregate a majority of the plurality of magnetic beads at a portion of the well, the second speed different from the first speed, wherein the rotation of the microtiter plate at the second speed produces a relative centrifugal force that does not exceed the magnetic force between the magnetic beads in a well of the microtiter plate and the magnetic structure.

16. The method of claim 15, wherein the first speed is in the range of about 800 rotations per minute to about 1,250 rotations per minute.

17. The method of claim 15, wherein the first duration is in the range of about 20 seconds to about 40 seconds.

18. The method of claim 15, wherein the first speed is in the range of about 800 rotations per minute to about 1,250 rotations per minute and the first duration is in the range of about 20 seconds to about 40 seconds.

19. The method of claim 15, wherein the second speed is in the range of about 400 rotations per minute to about 600 rotations per minute.

20. The method of claim 15, wherein the second duration is in the range of about 50 seconds to about 70 seconds.

21. The method of claim 15, wherein the second speed is in the range of about 400 rotations per minute to about 600 rotations per minute and the second duration is in the range of about 50 seconds to about 70 seconds.

22. The method of claim 15, further comprising:
   removing a portion of the contents in the well of the microtiter plate from the well of the microtiter plate following rotating the microtiter plate at the second speed for the second duration.

23. The method of claim 22, wherein the portion of the well in which the majority of magnetic beads are aggregated is a first portion of the well, and wherein the contents are removed from a second portion of the well away from the first portion.

24. The method of claim 15, wherein the sample is a biological sample.

25. The method of claim 24, wherein the biological sample is a blood sample.

26. The method of claim 24, wherein the biological sample contains a nucleic acid or a protein.

27. The method of claim 15, wherein an agent that specifically binds to a nucleic acid or a protein in the sample is immobilized to the surface of a magnetic bead.

* * * * *